United States Patent
Begley et al.

(10) Patent No.: US 7,087,320 B2
(45) Date of Patent: *Aug. 8, 2006

(54) ORGANIC ELEMENT FOR ELECTROLUMINESCENT DEVICES

(75) Inventors: William J. Begley, Rochester, NY (US); Tukaram K. Hatwar, Penfield, NY (US); Manju Rajeswaran, Fairport, NY (US); Natasha Andrievsky, Webster, NY (US)

(73) Assignee: Eastman Kodak Company, Rochester, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/700,894

(22) Filed: Nov. 4, 2003

(65) Prior Publication Data
US 2005/0095450 A1 May 5, 2005

(51) Int. Cl.
H05B 33/14 (2006.01)
H01L 51/50 (2006.01)
H01L 51/52 (2006.01)
H01L 51/54 (2006.01)
H01L 27/32 (2006.01)

(52) U.S. Cl. ............ 428/690; 428/917; 313/504; 313/506; 313/112; 427/66; 257/98

(58) Field of Classification Search ........ 428/690, 428/917; 313/504, 506, 112; 257/98; 427/66
See application file for complete search history.

(56) References Cited

U.S. PATENT DOCUMENTS

| 6,387,547 B1 | 5/2002 | Fujita et al. |
| 6,399,223 B1 | 6/2002 | Fujita et al. |
| 2002/0121638 A1 | 9/2002 | Grushin et al. |
| 2003/0099860 A1 * | 5/2003 | Lin et al. .......... 428/690 |

FOREIGN PATENT DOCUMENTS

| EP | 1 148 109 | 10/2001 |
| JP | 04-335087 | 11/1992 |
| JP | 10-289786 | 10/1998 |
| JP | 2000-156290 | 6/2000 |

(Continued)

OTHER PUBLICATIONS

V. V. Grushin et al., New, Efficient Electroluminescent Materials Based on Orgnometallic Ir Complexes, Chem. Commun., pp. 1494-1495, Jul. 2001.

(Continued)

Primary Examiner—Dawn L. Garrett
(74) Attorney, Agent, or Firm—Arthur E. Kluegel

(57) ABSTRACT

Disclosed is an OLED device comprising a light-emitting layer (LEL) containing a host and an emitting dopant located between a cathode and an anode wherein the dopant is a naphthacene derivative represented by formula (I):

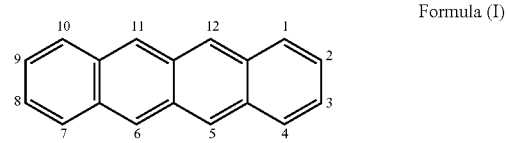

Formula (I)

wherein:
a) said naphthacene derivative contains at least one fluorine or fluorine containing group; and
b) when exactly two fluorine containing groups are present said groups are not located at the 5- and 12-positions or at the 6- and 11-positions.

33 Claims, 1 Drawing Sheet

FOREIGN PATENT DOCUMENTS

| | | | |
|---|---|---|---|
| JP | 2002-167578 | * | 6/2002 |
| WO | WO 02/100977 | | 12/2002 |
| WO | 03/010778 | | 2/2003 |

OTHER PUBLICATIONS

Co-pending, commonly assigned, concurrently filed, U.S. Appl. No. 10/701,040, filed Nov. 4, 2003 titled "Organic Element For Electroluminescent Devices", of Begley et al.

Co-pending, commonly assigned, concurrently filed, U.S. Appl. No. 10/700,916, filed Nov. 4, 2003 titled "Organic Element For Electroluminescent Devices", of Begley et al.

Co-pending, commonly assigned, concurrently filed, U.S. Appl. No. 10/701,241, filed Nov. 4, 2003 titled "Organic Element For Electroluminescent Devices", of Begley et al.

* cited by examiner

ORGANIC ELEMENT FOR ELECTROLUMINESCENT DEVICES

FIELD OF INVENTION

This invention relates to organic light emitting diode (OLED) electroluminescent (EL) device comprising a light-emitting layer containing a naphthacene dopant compound containing fluorine or fluorine-containing groups.

BACKGROUND OF THE INVENTION

While organic electroluminescent (EL) devices have been known for over two decades, their performance limitations have represented a barrier to many desirable applications. In simplest form, an organic EL device is comprised of an anode for hole injection, a cathode for electron injection, and an organic medium sandwiched between these electrodes to support charge recombination that yields emission of light. These devices are also commonly referred to as organic light-emitting diodes, or OLEDs. Representative of earlier organic EL devices are Gurnee et al. U.S. Pat. No. 3,172,862, issued Mar. 9, 1965; Gurnee U.S. Pat. No. 3,173,050, issued Mar. 9, 1965; Dresner, "Double Injection Electroluminescence in Anthracene", RCA Review, Vol. 30, pp. 322–334, 1969; and Dresner U.S. Pat. No. 3,710,167, issued Jan. 9, 1973. The organic layers in these devices, usually composed of a polycyclic aromatic hydrocarbon, were very thick (much greater than 1 μm). Consequently, operating voltages were very high, often >100V.

More recent organic EL devices include an organic EL element consisting of extremely thin layers (e.g. <1.0 μm) between the anode and the cathode. Herein, the organic EL element encompasses the layers between the anode and cathode electrodes. Reducing the thickness lowered the resistance of the organic layer and has enabled devices that operate at much lower voltage. In a basic two-layer EL device structure, described first in U.S. Pat. No. 4,356,429, one organic layer of the EL element adjacent to the anode is specifically chosen to transport holes, therefore, it is referred to as the hole-transporting layer, and the other organic layer is specifically chosen to transport electrons, referred to as the electron-transporting layer. The interface between the two layers provides an efficient site for the recombination of the injected hole/electron pair and the resultant electroluminescence.

There have also been proposed three-layer organic EL devices that contain an organic light-emitting layer (LEL) between the hole-transporting layer and electron-transporting layer, such as that disclosed by Tang et al [J. Applied Physics, Vol. 65, Pages 3610–3616, 1989]. The light-emitting layer commonly consists of a host material doped with a guest material—dopant, which results in an efficiency improvement and allows color tuning.

Since these early inventions, further improvements in device materials have resulted in improved performance in attributes such as color, stability, luminance efficiency and manufacturability, e.g., as disclosed in U.S. Pat. No. 5,061,569, U.S. Pat. No. 5,409,783, U.S. Pat. No. 5,554,450, U.S. Pat. No. 5,593,788, U.S. Pat. No. 5,683,823, U.S. Pat. No. 5,908,581, U.S. Pat. No. 5,928,802, U.S. Pat. No. 6,020,078, and U.S. Pat. No. 6,208,077, amongst others.

Notwithstanding these developments, there are continuing needs for organic EL device components, such as dopants, that will provide high luminance efficiencies combined with high color purity and long lifetimes.

A useful class of dopants is that derived from 5,6,11,12-tetraphenylnaphthacene, also referred to as rubrene. The solution spectra of these materials are typically characterized by wavelength of maximum emission, also referred to as emission $\lambda_{max}$, in a range of 550–560 nm and are useful in organic EL devices in combination with dopants in other layers to produce white light. Use of these rubrene-derived dopants in EL devices depends on whether the material sublimes. If the material melts, its use as a dopant is limited. Sublimation and deposition are the processes by which the dopant, subjected to high temperature and low pressure passes from the solid phase to the gas phase and back to the solid phase and in the process is deposited onto the device. Depending on the chemical structure of the dopant, when the temperature needed to sublime the dopant is high, thermal decomposition can occur. If the decomposition products also sublime the device can become contaminated. Decomposition leads to the inefficient use of dopant. Contamination with decomposition products can cause the device to have shorter operational lifetimes and can contribute to color degradation and light purity. In order to achieve OLEDs that can produce high purity white light, have good stability and no contamination from dopant decomposition, in addition to efficient use of dopant, one needs to have the ability to lower the sublimation temperature.

Useful dopants are those that emit light in ethyl acetate solution in the range of 530–650 nm, have good efficiency and sublime readily.

U.S. Pat. No. 6,387,547; U.S. Pat. No. 6,399,223; EP 1,148,109A2, and JP20001156290A teaches the use of rubrene derivatives containing either 2 phenyl groups on one end ring of the rubrene structure or 4 phenyl groups on both end rings. There is no teaching of fluorine or fluorine-containing groups on the rubrene structure.

JP 1998289786A discloses compound "15" with two fluorine-containing groups on the 5- and 12-positions of the naphthacene nucleus. Compound 15 falls outside the scope of the current invention.

WO 02/100977A1 discloses compound "C12" with two fluorine-containing groups also on the 5- and 12-positions of the naphthacene nucleus, but this too falls outside the scope of the current invention.

JP 04335087 discloses specific compounds 6, 13 and 14 containing chlorine or bromine at various positions on the rubrene molecule.

However, high sublimation temperatures and possible decomposition would limit the use of these rubrene derivatives. Thus devices containing these rubrene derivatives would fail to provide consistent white OLED devices with high color purity and reduced potential for possible contamination from decomposition impurities in their deposition.

The problem to be solved is to provide a dopant compound for a light-emitting layer of an OLED device that provides good luminance efficiency and low sublimation temperatures.

SUMMARY OF THE INVENTION

An OLED device comprising a light-emitting layer (LEL) containing a host and an emitting dopant located between a cathode and an anode wherein the dopant is a naphthacene derivative represented by formula (I):

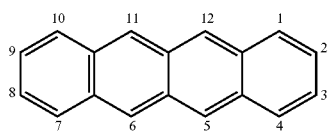

Formula (I)

wherein:
a) said naphthacene derivative contains at least one fluorine or fluorine containing group; and
b) when exactly two fluorine containing groups are present said groups are not located at the 5- and 12-positions or at the 6- and 11-positions.

The invention also provides a display including such a device and a method of imaging using such a device.

Such a device exhibits electroluminescence emitting yellow-orange or orange-red light with good luminance efficiency and low sublimation temperatures.

DETAILED DESCRIPTION OF THE INVENTION

Figure 1:
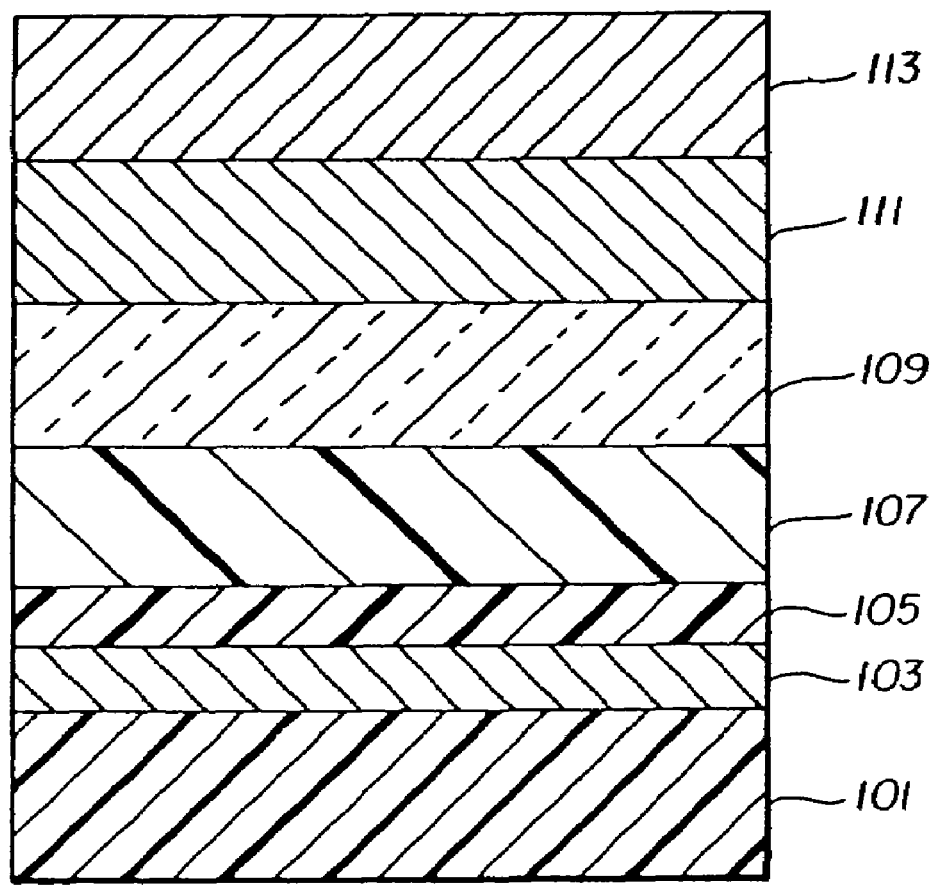
FIG. 1 shows a cross-section of a typical OLED device in which this invention may be used.

The invention is generally as described above.

An OLED device of the invention is a multilayer electroluminescent device comprising a cathode, an anode, charge-injecting layers (if necessary), charge-transporting layers, and a light-emitting layer (LEL) comprising a host and at least one light emitting dopant, a naphthacene compound. The term naphthacene is the chemical name used to describe four linearly fused benzene rings as defined by the *Grant & Hackh's Chemical Dictionary*, Fifth Edition, McGraw-Hill Book Company, page 383. The term rubrene refers to a 5,6,11,12-tetraphenylnaphthacene as defined by the *Grant & Hackh's Chemical Dictionary*, Fifth Edition, McGraw-Hill Book Company, page 512 and *Dictionary of Organic Compounds*, Fifth Edition, Chapman and Hall, Volume 5, page 5297.

Suitably, the light-emitting layer of the device comprises a host and light emitting dopant where the dopant is present in an amount of up to 10%-wt of the host, more typically from 0.1–5.0%-wt of the host. The dopant is suitably a naphthacene containing one or more fluorine or fluorine-containing groups, and usefully a 5,6,11,12-tetraphenyl-naphthacene containing one or more fluorine or fluorine-containing groups. Good results are obtained when the phenyl groups are substituted, particularly where the substituent groups are fluorine, fluorine containing groups, alkyl, aryl, alkoxy or aryloxy groups.

Useful dopants of the invention are those that emit light in ethyl acetate solution such that $520 \text{ nm} \leq \lambda_{max} \leq 650 \text{ nm}$ and preferable $530 \text{ nm} \leq \lambda_{max} \leq 625 \text{ nm}$, have good efficiency and sublime at low temperatures. Combined with other light emitting dopants, the dopants of the invention can be used to produce white light. The other light emitting dopants are usefully dopants that emit blue or blue-green light.

Blue light is generally defined as having a wavelength range in the visible region of the electromagnetic spectrum of 450–480 nm, blue-green 480–510 nm, green 510–550, green-yellow 550–570 nm, yellow 570–590 nm, orange 590–630 nm and red 630–700 mn, as defined by Dr. R. W. G. Hunt in *The Reproduction of Colour in Photography, Printing & Television*, 4$^{th}$ Edition 1987, Fountain Press, page 4. Suitable combinations of these components produce white light. When light has a spectral profile that overlaps these ranges, to whatever degree, it is loosely referred to as having both color components for example, yellow-orange or orange-red.

Another embodiment of the invention comprises additional layers incorporating dopants the light from which in combination with the light of the naphthacene derivative combine to give white light. Such additional dopants can be chosen so that they emit blue or blue-green light.

In another embodiment of the invention when additional layers are present so that the emitted light is white, a filter capable of controlling the spectral components of the white light such as red, green and blue, can be placed over-lying the device to give a device useful for color display. Suitably, each light-emitting layer of the device comprises a host and dopant where the dopant is present in an amount of up to 10%-wt of the host, more typically from 0.1–5.0%-wt of the host The benefit imparted by the dopant does not appear to be host specific. Desirable hosts include those based on amine compounds. One particularly example of a host is N,N'-di-1-naphthalenyl-N,N'-diphenyl-4,4'-diaminobiphenyl (NPB)

Embodiments of the dopants useful in the invention provide an EL device emitting light with yellow, yellow-orange, orange, orange-red or red hues. In combination with the dopants of the invention, additional dopants that emit blue or blue-green light in additional layers, results in the formation of white light. Substituents on the dopants of the invention are selected to provide embodiments that exhibit a reduced loss of initial luminance compared to the device containing no naphthacene compound.

Useful naphthacene derivatives of the invention are dopants that have either sublimation temperatures lower by at least 5° C. to 20° C. than the naphthacene derivative without fluorine or fluorine containing groups, or they sublime, whereas the derivative without the fluorine or fluorine containing groups melts. Lower sublimation temperatures reduce the possibility that the dopants will decompose. Lower quality devices result when dopants melt before they are deposited on the device.

Formula (II) suitably represents compounds useful in the invention:

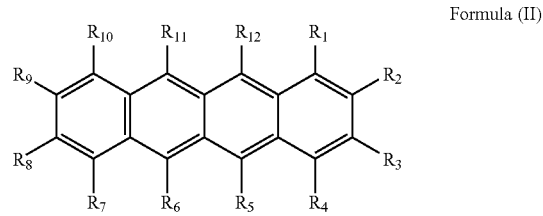

Formula (II)

wherein:
at least one of $R_1$ through $R_{12}$ is fluorine or a fluorine containing group:
provided that the remaining $R_1$ through $R_{12}$ are selected from hydrogen and substituent groups, and at least one of which is a phenyl group; and
provided further that when exactly two fluorine containing groups are present said groups are not located at $R_5$ and $R_{12}$ or at $R_6$ and $R_{11}$.

When $R_5$, $R_6$, $R_{11}$ and $R_{12}$ of Formula (II) are phenyl groups, particularly useful compounds of the invention are represented by formula (III):

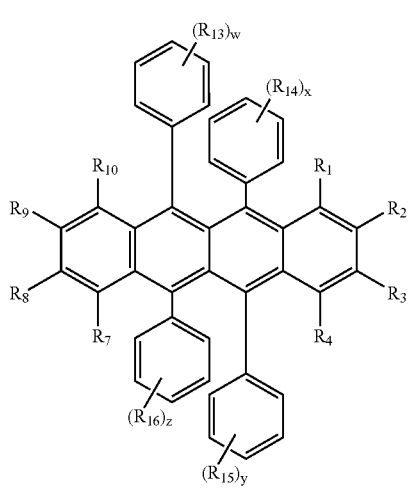

Formula (III)

wherein:
W, X, Y and Z are independently 0–5;
at least one of $R_1$, $R_2$, $R_3$, $R_4$, $R_7$, $R_8$, $R_9$, $R_{10}$, $R_{13}$, $R_{14}$, $R_{15}$, and $R_{16}$ is fluorine or a fluorine containing group:
provided that the remaining $R_1$, $R_2$, $R_3$, $R_4$, $R_7$, $R_8$, $R_9$, $R_{10}$, $R_{13}$, $R_{14}$, $R_{15}$, and $R_{16}$ are selected from substituent groups; and
provided further that when exactly two fluorine or fluorine containing groups are present said groups are not located at $R_{14}$ and $R_{15}$ or at $R_{13}$ and $R_{16}$.

Further useful embodiments of the invention when $R_1$, $R_4$, $R_7$, and $R_{10}$ of Formula (II) are hydrogen, are represented by formula (IV):

Formula (IV)

wherein:
W, X, Y and Z are independently 0–5;
at least one of $R_2$, $R_3$, $R_8$, $R_9$, $R_{13}$, $R_{14}$, $R_{15}$, and $R_{16}$ is fluorine or a fluorine containing group:
provided that the remaining $R_2$, $R_3$, $R_8$, $R_9$, $R_{13}$, $R_{14}$, $R_{15}$, and $R_{16}$ are selected from substituent groups;
provided further that when exactly two fluorine or fluorine containing groups are present said groups are not located at $R_{14}$ and $R_{15}$ or at $R_{13}$ and $R_{16}$.

Still further useful embodiments of the invention when $R_1$ through $R_4$, and $R_7$ through $R_{10}$ of Formula (II) are hydrogen, are represented by formula (V):

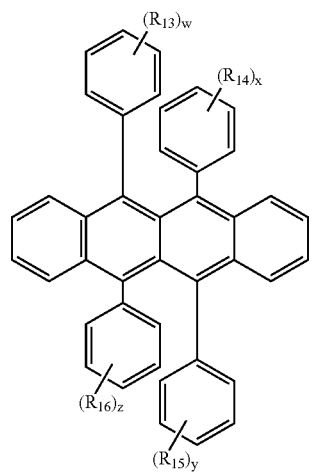

Formula (V)

wherein:
W, X, Y and Z are independently 0–5;
at least one of $R_{13}$, $R_{14}$, $R_{15}$, and $R_{16}$ is fluorine or a fluorine containing group;
provided that the remaining $R_{13}$, $R_{14}$, $R_{15}$, and $R_{16}$ are selected from substituent groups;
provided further that when exactly two fluorine or fluorine containing groups are present said groups are not located at $R_{14}$ and $R_{15}$ or at $R_{13}$ and $R_{16}$.

Formula (VI) represents symmetrically substituted light emitting dopants of the invention where the diagonally opposite phenyl groups contain identical substituents:

Formula (VI)

wherein:
$R_{18}$, is fluorine or a fluorine containing group:
$R_{17}$ is a substituent;
m is 0–5.

In formulae (II) through (VI) useful in the device, the $R_1$ through $R_{18}$ groups are conveniently selected from hydrogen fluorine, alkyl, alkoxy, carbocyclic and heterocyclic groups with at least one fluorine group present. The carbocyclic and heterocyclic groups can be aromatic or non-aromatic, but particularly useful are aromatic carbocyclic groups. The fluorine can be attached directly to the naphthacene nucleus or it can be part of another substituent that is in turn attached to the naphthacene. When part of another substituent, the substituent is referred to as a fluorine-containing group. The fluorine can be attached to an alkyl group or attached to a phenyl group. Particularly useful fluorinated alkyl groups are trifluoromethyl and pentafluoroethyl groups. Particularly useful fluorinated-phenyl groups contain 1–5 fluorine atoms and these fluorine atoms can be located in the ortho, meta or para positions in any combination, or in all such positions. The alkyl groups can be branched or linear, but preferred alkyl groups are methyl, ethyl, propyl, n-butyl and tert-butyl. There can be 1–30 fluorine atoms present in the dopants of the invention with up to 5 fluorine atoms located on a single phenyl group, or a phenyl group may contain a single fluorine atom with other non-fluorinated groups in the other positions, or the fluorine atoms can be distributed over the $R_1$ through $R_{18}$ groups. Preferred positions for locating the fluorine or fluorine-containing groups are on $R_5$, $R_6$, $R_{11}$ and $R_{12}$ and when exactly 2 fluorine atoms are present they are not $R_{13}$ and $R_{16}$ or $R_{14}$ and $R_{15}$. Particularly useful positions for locating the fluorine or fluorine-containing groups are on the diagonally opposite positions $R_5$ and $R_{11}$ or $R_6$ and $R_{12}$. The term "diagonally opposite positions" refers to the location of the $R_5$ and $R_{11}$, or $R_6$ and $R_{12}$ on the naphthacene nucleus. These groups are diagonally opposite each other The emission wavelength of these compounds may be adjusted to some extent by appropriate changes to $R_1$, $R_2$, $R_3$, $R_4$, $R_5$, $R_6$ and $R_7$ groups to meet a color aim, namely orange-red.

The naphthacene compound is usually doped into a host compound, which represents the light-emitting layer between the hole-transporting and electron-transporting layers. The host is chosen such that there is efficient energy transfer from the host to the naphthacene compound. The naphthacene compound emits from the excited state to afford a bright, highly efficient, stable EL device.

The EL device of the invention is useful in any device where light emission is desired such as a lamp or a component in a static or motion imaging device, such as a television, cell phone, DVD player, or computer monitor.

Illustrative examples of rubrene compounds useful in the present invention are the following:

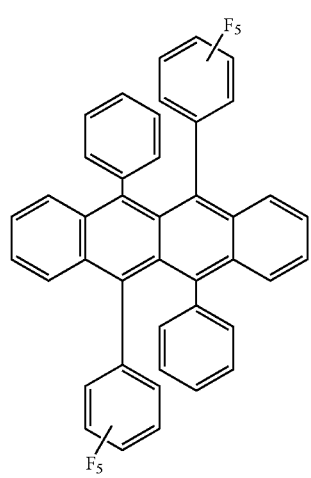

Inv-1

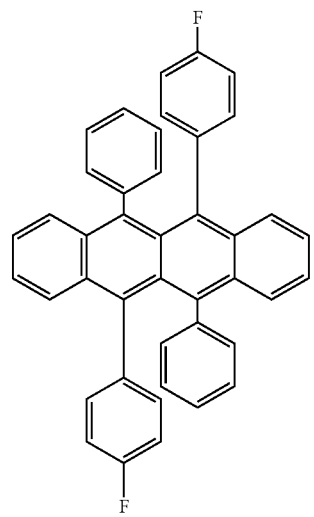

Inv-2

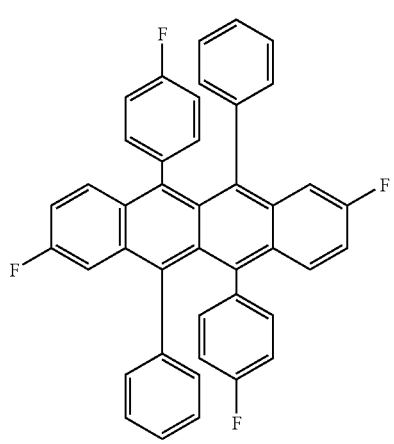

Inv-3

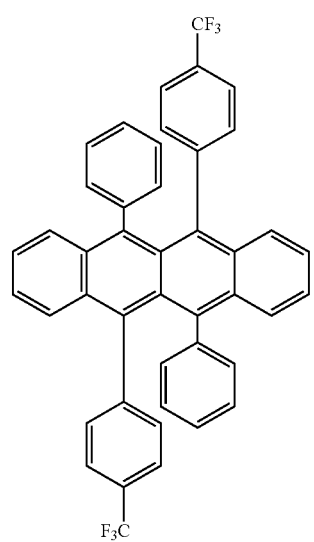

Inv-4

-continued
Inv-5
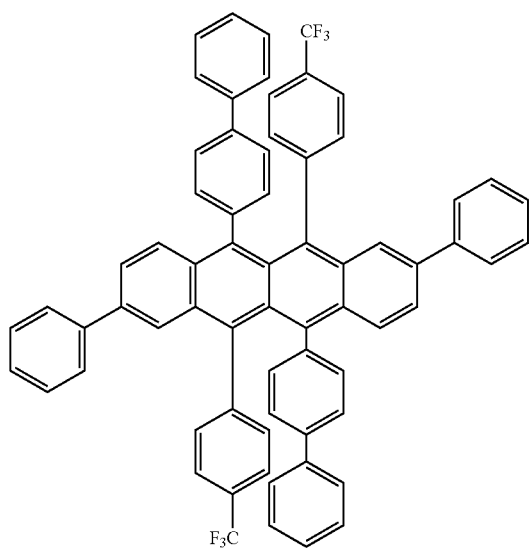
Inv-6
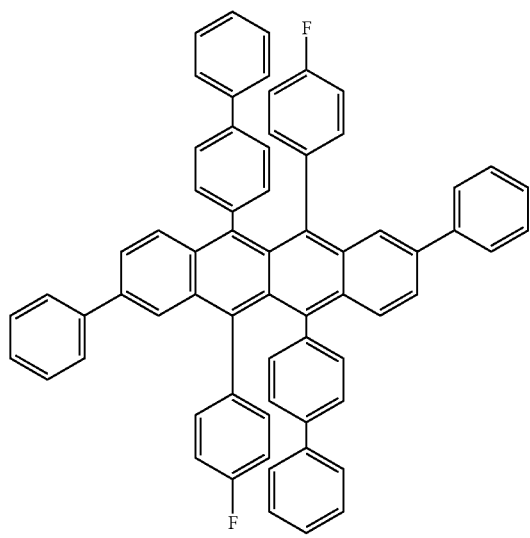
-continued
Inv-7
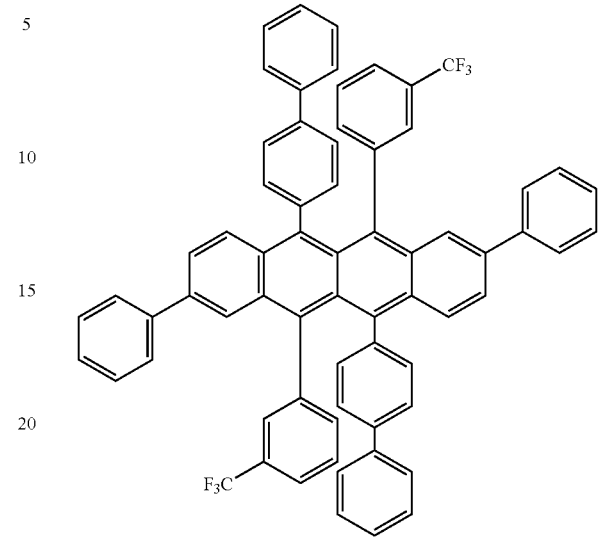
Inv-8

-continued
Inv-9
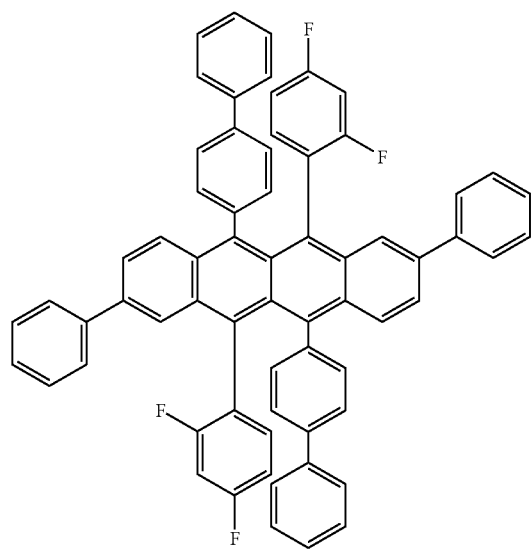
Inv-11
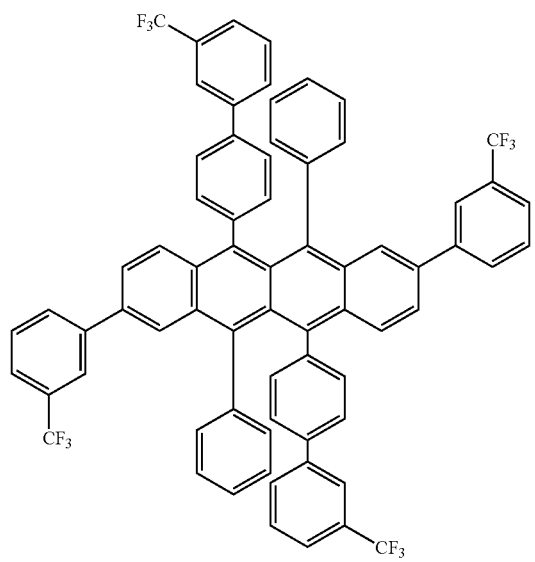
Inv-10
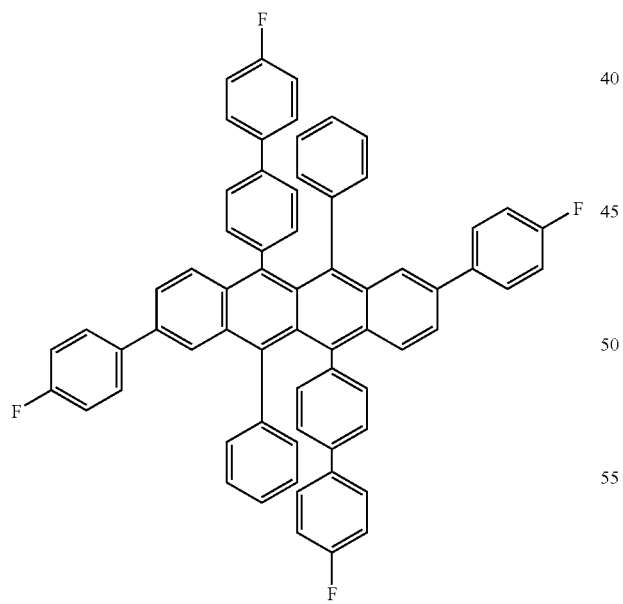
Inv-12
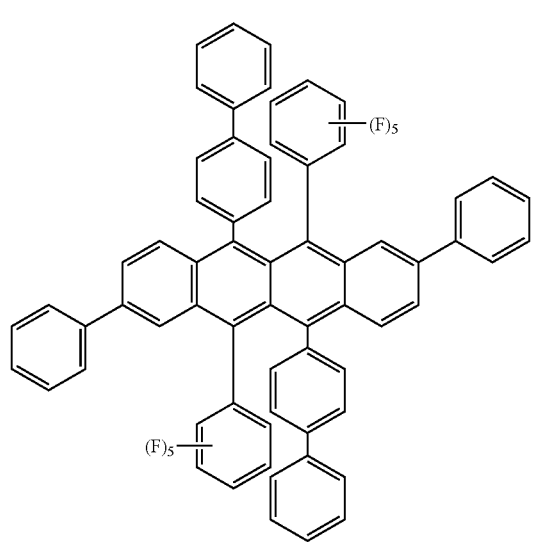

-continued
Inv-13
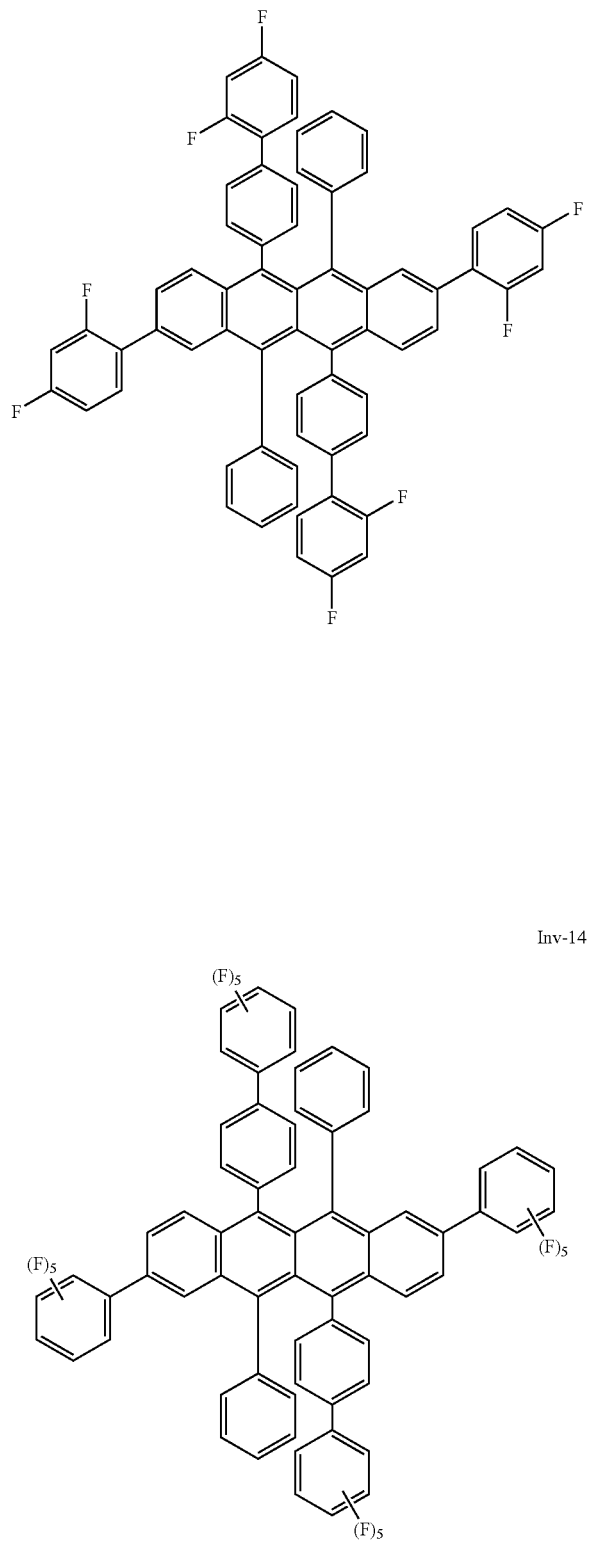
Inv-14
Inv-15
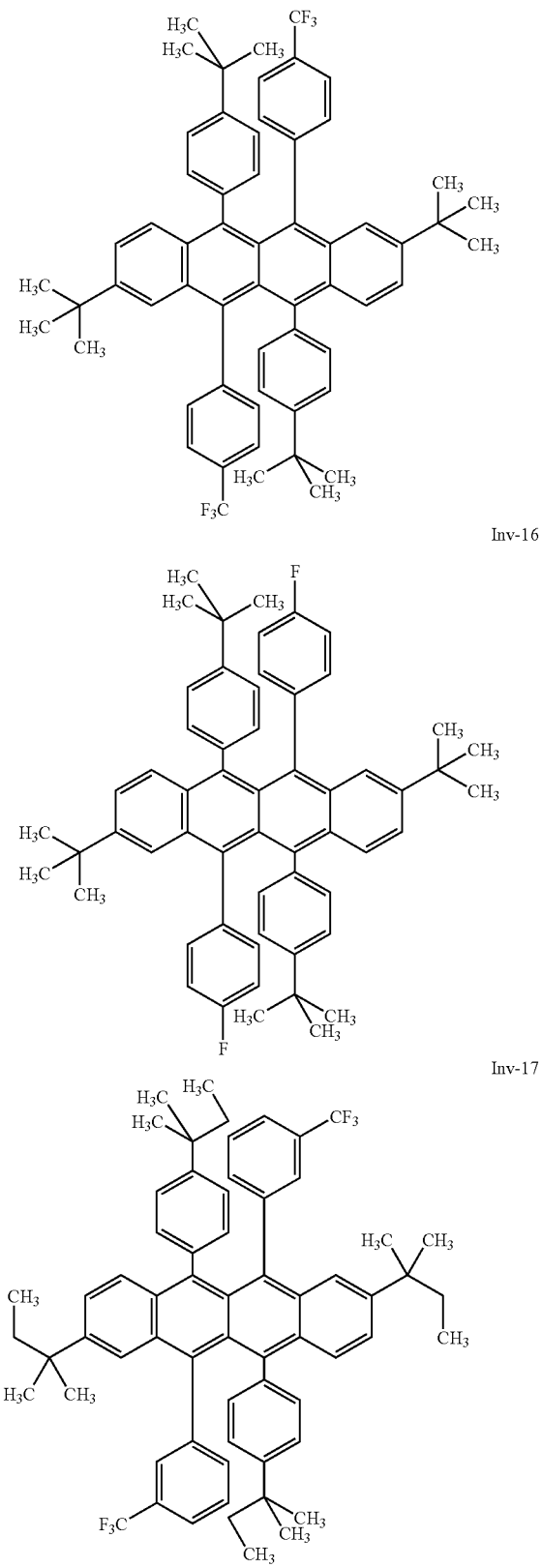
Inv-16
Inv-17

Inv-18
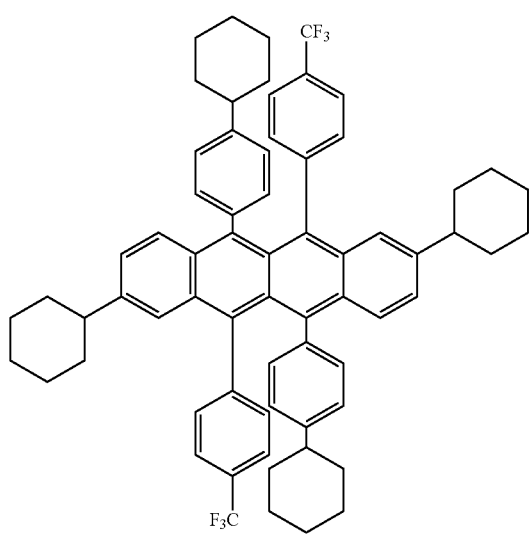
Inv-19
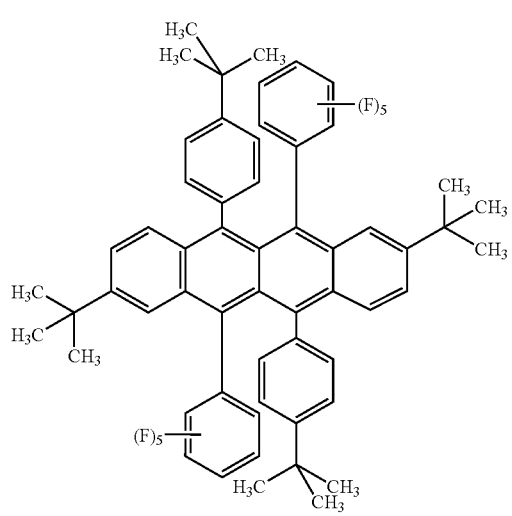
Inv-20
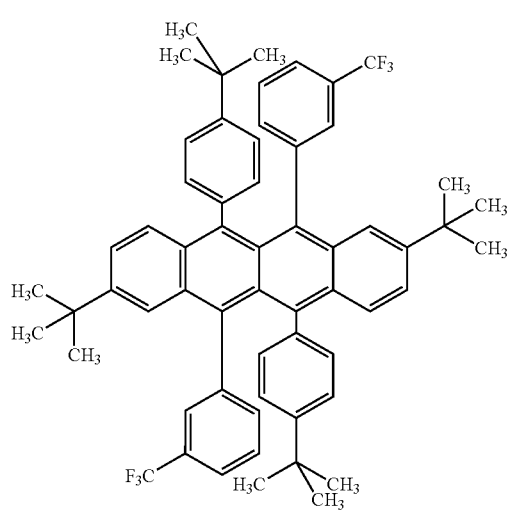
Inv-21
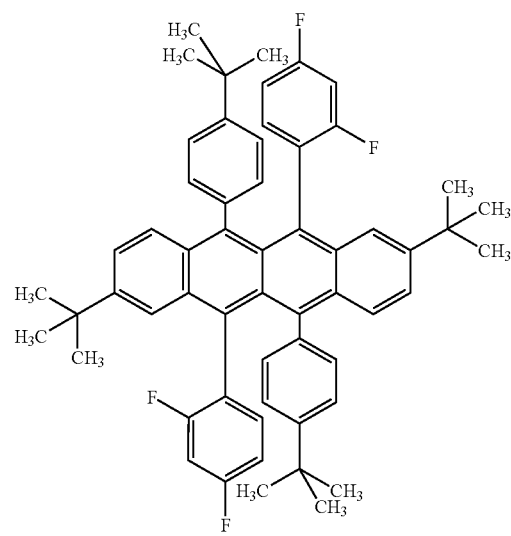
Inv-22
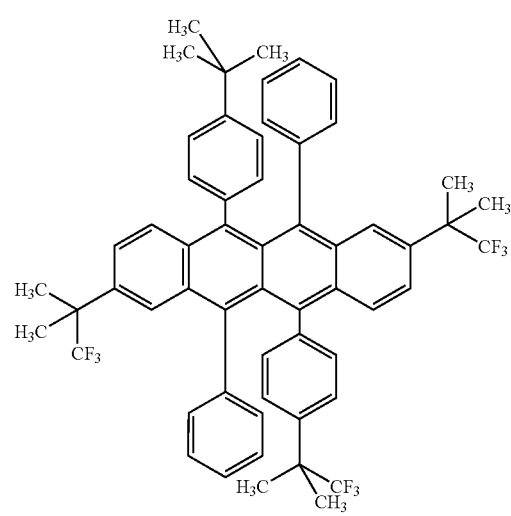
Inv-23
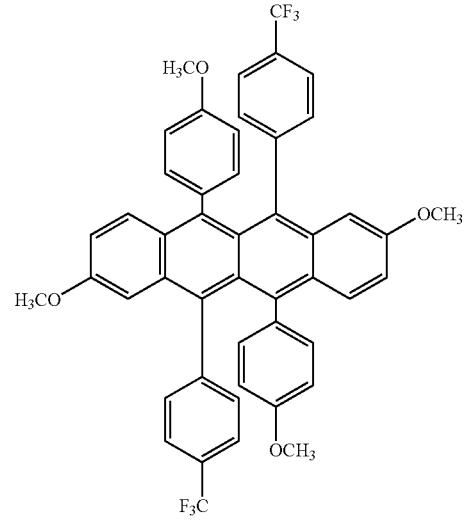

-continued
Inv-24
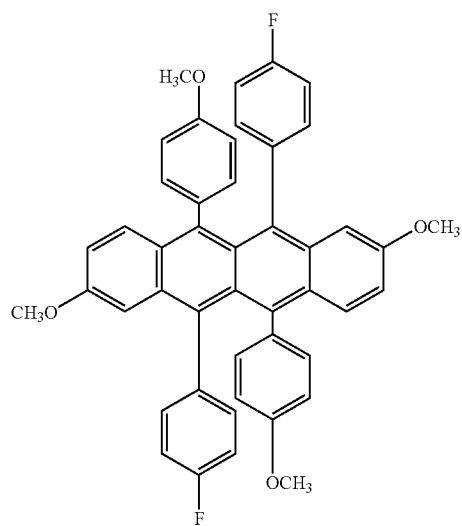
Inv-25
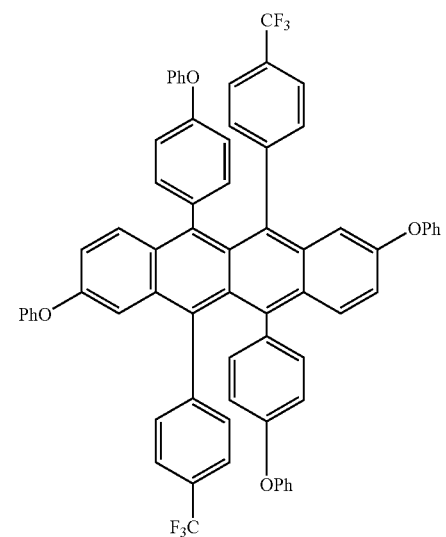
Inv-26
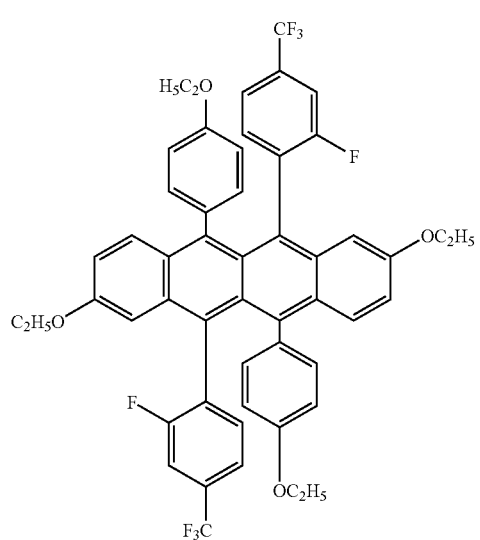
-continued
Inv-27
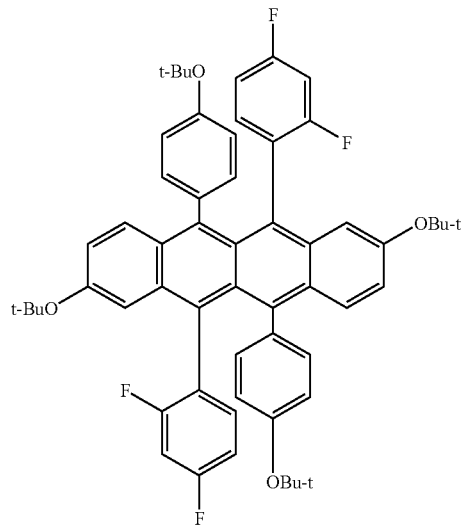
Inv-28
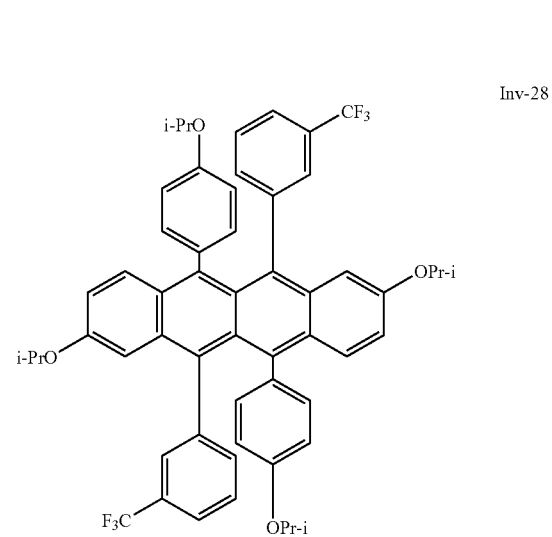
Inv-29
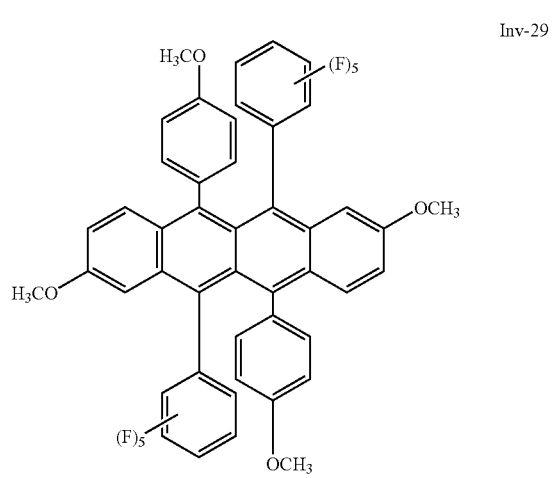

-continued

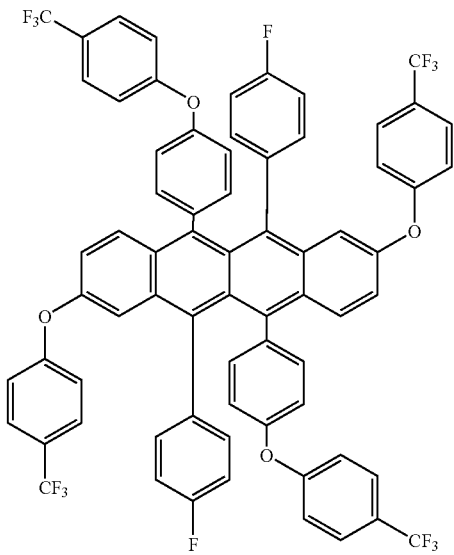
Inv-30

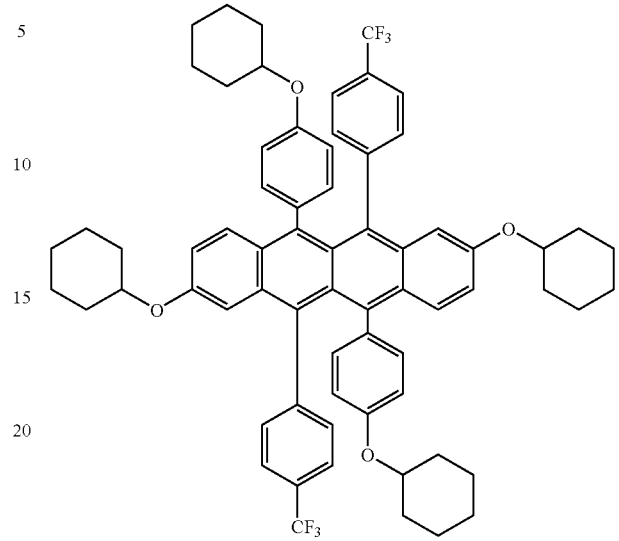
Inv-33

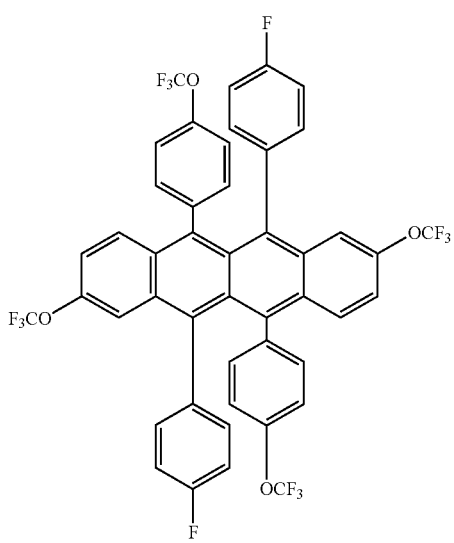
Inv-31

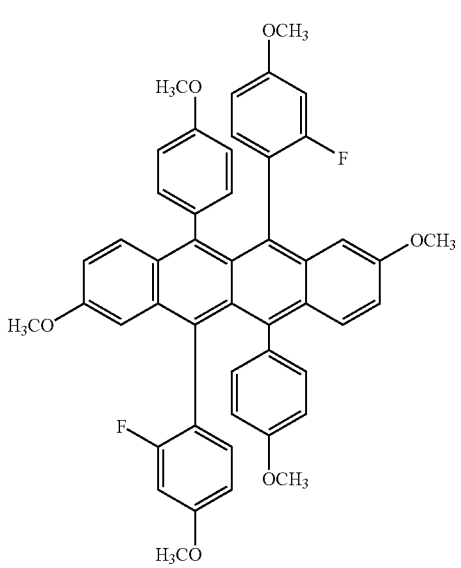
Inv-34

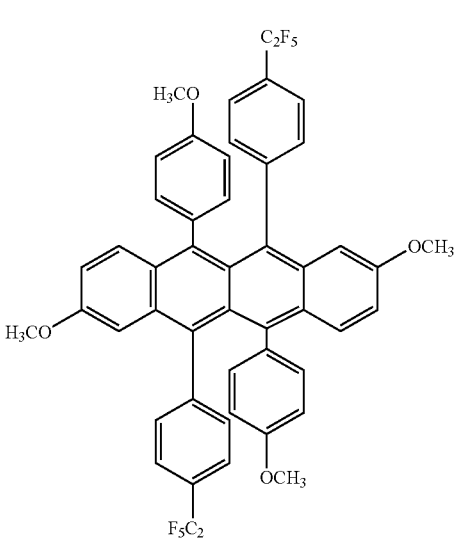
Inv-32

Embodiments of the invention provide not only emission of visible light in the yellow, orange and red regions of the visible spectrum but also high luminance efficiency and a more desirable lowering of the sublimation temperature as evidenced by the comparisons to dopants without the embodiments of the invention.

Unless otherwise specifically stated, use of the term "substituted" or "substituent" means any group or atom other than hydrogen. Additionally, when the term "group" is used, it means that when a substituent group contains a substitutable hydrogen, it is also intended to encompass not only the substituent's unsubstituted form, but also its form further substituted with any substituent group or groups as herein mentioned, so long as the substituent does not destroy properties necessary for device utility. Suitably, a substituent group may be halogen or may be bonded to the remainder of the molecule by an atom of carbon, silicon, oxygen, nitrogen, phosphorous, sulfur, selenium, or boron. The substituent may be, for example, halogen, such as chloro, bromo or fluoro; nitro; hydroxyl; cyano; carboxyl; or groups which may be further substituted, such as alkyl, including straight or branched chain or cyclic alkyl, such as methyl, trifluoromethyl, ethyl, t-butyl, 3-(2,4-di-t-pentylphenoxy) propyl, and tetradecyl; alkenyl, such as ethylene, 2-butene; alkoxy, such as methoxy, ethoxy, propoxy, butoxy, 2-methoxyethoxy, sec-butoxy, hexyloxy, 2-ethylhexyloxy, tetradecyloxy, 2-(2,4-di-t-pentylphenoxy)ethoxy, and 2-dodecyloxyethoxy; aryl such as phenyl, 4-t-butylphenyl, 2,4,6-trimethylphenyl, naphthyl; aryloxy, such as phenoxy, 2-methylphenoxy, alpha- or beta-naphthyloxy, and 4-tolyloxy; carbonamido, such as acetamido, benzamido, butyramido, tetradecanamido, alpha-(2,4-di-t-pentyl-phenoxy)acetamido, alpha-(2,4-di-t-pentylphenoxy)butyramido, alpha-(3-pentadecylphenoxy)-hexanamido, alpha-(4-hydroxy-3-t-butylphenoxy)-tetradecanamido, 2-oxo-pyrrolidin-1-yl, 2-oxo-5-tetradecylpyrrolin-1-yl, N-methyltetradecanamido, N-succinimido, N-phthalimido, 2,5-dioxo-1-oxazolidinyl, 3-dodecyl-2,5-dioxo-1-imidazolyl, and N-acetyl-N-dodecylamino, ethoxycarbonylamino, phenoxycarbonylamino, benzyloxycarbonylamino, hexadecyloxycarbonylamino, 2,4-di-t-butylphenoxycarbonylamino, phenylcarbonylamino, 2,5-(di-t-pentylphenyl)carbonylamino, p-dodecyl-phenylcarbonylamino, p-tolylcarbonylamino, N-methylureido, N,N-dimethylureido, N-methyl-N-dodecylureido, N-hexadecylureido, N,N-dioctadecylureido, N,N-dioctyl-N'-ethylureido, N-phenylureido, N,N-diphenylureido, N-phenyl-N-p-tolylureido, N-(m-hexadecylphenyl)ureido, N,N-(2,5-di-t-pentylphenyl)-N'-ethylureido, and t-butylcarbonamido; sulfonamido, such as methylsulfonamido, benzenesulfonamido, p-tolylsulfonamido, p-dodecylbenzenesulfonamido, N-methyltetradecylsulfonamido, N,N-dipropyl-sulfamoylamino, and hexadecylsulfonamido; sulfamoyl, such as N-methylsulfamoyl, N-ethylsulfamoyl, N,N-dipropylsulfamoyl, N-hexadecylsulfamoyl, N,N-dimethylsulfamoyl, N-[3-(dodecyloxy)propyl]sulfamoyl, N-[4-(2,4-di-t-pentylphenoxy)butyl]sulfamoyl, N-methyl-N-tetradecylsulfamoyl, and N-dodecylsulfamoyl; carbamoyl, such as N-methylcarbamoyl, N,N-dibutylcarbamoyl, N-octadecylcarbamoyl, N-[4-(2,4-di-t-pentylphenoxy)butyl]carbamoyl, N-methyl-N-tetradecylcarbamoyl, and N,N-dioctylcarbamoyl; acyl, such as acetyl, (2,4-di-t-amylphenoxy)acetyl, phenoxycarbonyl, p-dodecyloxyphenoxycarbonyl methoxycarbonyl, butoxycarbonyl, tetradecyloxycarbonyl, ethoxycarbonyl, benzyloxycarbonyl, 3-pentadecyloxycarbonyl, and dodecyloxycarbonyl; sulfonyl, such as methoxysulfonyl, octyloxysulfonyl, tetradecyloxysulfonyl, 2-ethylhexyloxysulfonyl, phenoxysulfonyl, 2,4-di-t-pentylphenoxysulfonyl, methylsulfonyl, octylsulfonyl, 2-ethylhexylsulfonyl, dodecylsulfonyl, hexadecylsulfonyl, phenylsulfonyl, 4-nonylphenylsulfonyl, and p-tolylsulfonyl; sulfonyloxy, such as dodecylsulfonyloxy, and hexadecylsulfonyloxy; sulfinyl, such as methylsulfinyl, octylsulfinyl, 2-ethylhexylsulfinyl, dodecylsulfinyl, hexadecylsulfinyl, phenylsulfinyl, 4-nonylphenylsulfinyl, and p-tolylsulfinyl; thio, such as ethylthio, octylthio, benzylthio, tetradecylthio, 2-(2,4-di-t-pentylphenoxy)ethylthio, phenylthio, 2-butoxy-5-t-octylphenylthio, and p-tolylthio; acyloxy, such as acetyloxy, benzoyloxy, octadecanoyloxy, p-dodecylamidobenzoyloxy, N-phenylcarbamoyloxy, N-ethylcarbamoyloxy, and cyclohexylcarbonyloxy; amine, such as phenylanilino, 2-chloroanilino, diethylamine, dodecylamine; imino, such as 1 (N-phenylimido)ethyl, N-succinimido or 3-benzylhydantoinyl; phosphate, such as dimethylphosphate and ethylbutylphosphate; phosphite, such as diethyl and dihexylphosphite; a heterocyclic group, a heterocyclic oxy group or a heterocyclic thio group, each of which may be substituted and which contain a 3 to 7 membered heterocyclic ring composed of carbon atoms and at least one hetero atom selected from the group consisting of oxygen, nitrogen, sulfur, phosphorous, or boron. such as 2-furyl, 2-thienyl, 2-benzimidazolyloxy or 2-benzothiazolyl; quaternary ammonium, such as triethylammonium; quaternary phosphonium, such as triphenylphosphonium; and silyloxy, such as trimethylsilyloxy.

If desired, the substituents may themselves be further substituted one or more times with the described substituent groups. The particular substituents used may be selected by those skilled in the art to attain the desired desirable properties for a specific application and can include, for example, electron-withdrawing groups, electron-donating groups, and steric groups. When a molecule may have two or more substituents, the substituents may be joined together to form a ring such as a fused ring unless otherwise provided. Generally, the above groups and substituents thereof may include those having up to 48 carbon atoms, typically 1 to 36 carbon atoms and usually less than 24 carbon atoms, but greater numbers are possible depending on the particular substituents selected.

General Device Architecture

The present invention can be employed in most OLED device configurations. These include very simple structures comprising a single anode and cathode to more complex devices, such as passive matrix displays comprised of orthogonal arrays of anodes and cathodes to form pixels, and active-matrix displays where each pixel is controlled independently, for example, with a thin film transistor (TFT).

There are numerous configurations of the organic layers wherein the present invention can be successfully practiced. Essential requirements are a cathode, an anode, an HTL and an LEL. A more typical structure is shown in FIG. 1 and contains a substrate 101, an anode 103, an optional hole-injecting layer 105, a hole-transporting layer 107, a light-emitting layer 109, an electron-transporting layer 111, and a cathode 113. These layers are described in detail below. Note that the substrate may alternatively be located adjacent to the cathode, or the substrate may actually constitute the anode or cathode. Also, the total combined thickness of the organic layers is preferably less than 500 nm.

Substrate

The substrate 101 can either be light transmissive or opaque, depending on the intended direction of light emission. The light transmissive property is desirable for viewing the EL emission through the substrate. Transparent glass or organic materials are commonly employed in such cases. For applications where the EL emission is viewed through the top electrode, the transmissive characteristic of the bottom support is immaterial, and therefore can be light transmissive, light absorbing or light reflective. Substrates for use in this case include, but are not limited to, glass, plastic, semiconductor materials, ceramics, and circuit board materials. Of course it is necessary to provide in these device configurations a light-transparent top electrode.

Anode

The conductive anode layer 103 is commonly formed over the substrate and, when EL emission is viewed through the anode, should be transparent or substantially transparent to the emission of interest. Common transparent anode materials used in this invention are indium-tin oxide (ITO) and tin oxide, but other metal oxides can work including, but not limited to, aluminum- or indium-doped zinc oxide (IZO), magnesium-indium oxide, and nickel-tungsten oxide.

In addition to these oxides, metal nitrides, such as gallium nitride, and metal selenides, such as zinc selenide, and metal sulfides, such as zinc sulfide, can be used in layer 103. For applications where EL emission is viewed through the top electrode, the transmissive characteristics of layer 103 are immaterial and any conductive material can be used, transparent, opaque or reflective. Example conductors for this application include, but are not limited to, gold, iridium, molybdenum, palladium, and platinum. Typical anode materials, transmissive or otherwise, have a work function of 4.1 eV or greater. Desired anode materials are commonly deposited by any suitable means such as evaporation, sputtering, chemical vapor deposition, or electrochemical means. Anodes can be patterned using well-known photolithographic processes.

Hole-Injecting Layer (HIL)

While not always necessary, it is often useful that a hole-injecting layer 105 be provided between anode 103 and hole-transporting layer 107. The hole-injecting material can serve to improve the film formation property of subsequent organic layers and to facilitate injection of holes into the hole-transporting layer. Suitable materials for use in the hole-injecting layer include, but are not limited to, porphyrinic compounds such as those described in U.S. Pat. No. 4,720,432, and plasma-deposited fluorocarbon polymers such as those described in U.S. Pat. No. 6,208,075. Alternative hole-injecting materials reportedly useful in organic EL devices are described in EP 0 891 121 A1 and EP 1 029 909 A1.

Hole-Transporting Layer (HTL)

The hole-transporting layer 107 of the organic EL device contains at least one hole-transporting compound such as an aromatic tertiary amine, where the latter is understood to be a compound containing at least one trivalent nitrogen atom that is bonded only to carbon atoms, at least one of which is a member of an aromatic ring. In one form the aromatic tertiary amine can be an arylamine, such as a monoarylamine, diarylamine, triarylamine, or a polymeric arylamine group. Exemplary monomeric triarylamines are illustrated by Klupfel et al. U.S. Pat. No. 3,180,730. Other suitable triarylamines substituted with one or more vinyl radicals and/or comprising at least one active hydrogen containing group are disclosed by Brantley et al U.S. Pat. No. 3,567,450 and U.S. Pat. No. 3,658,520.

A more preferred class of aromatic tertiary amines are those which include at least two aromatic tertiary amine moieties as described in U.S. Pat. No. 4,720,432 and U.S. Pat. No. 5,061,569. Such compounds include those represented by structural formula (A).

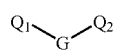

A wherein $Q_1$ and $Q_2$ are independently selected aromatic tertiary amine moieties and G is a linking group such as an arylene, cycloalkylene, or alkylene group of a carbon to carbon bond. In one embodiment, at least one of $Q_1$ or $Q_2$ contains a polycyclic fused ring group, e.g., a naphthalene. When G is an aryl group, it is conveniently a phenylene, biphenylene, or naphthalene group.

A useful class of triarylamine groups satisfying structural formula (A) and containing two triarylamine groups is represented by structural formula (B):

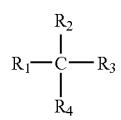

B where
$R_1$ and $R_2$ each independently represents a hydrogen atom, an aryl group, or an alkyl group or $R_1$ and $R_2$ together represent the atoms completing a cycloalkyl group; and
$R_3$ and $R_4$ each independently represents an aryl group, which is in turn substituted with a diaryl substituted amino group, as indicated by structural formula (C):

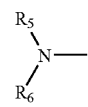

C wherein $R_5$ and $R_6$ are independently selected aryl groups. In one embodiment, at least one of $R_5$ or $R_6$ contains a polycyclic fused ring group, e.g., a naphthalene.

Another class of aromatic tertiary amine groups is the tetraaryldiamines. Desirable tetraaryldiamines groups include two diarylamino groups, such as indicated by formula (C), and linked through an arylene group. Useful tetraaryldiamines include those represented by formula (D).

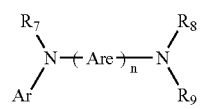

D wherein
each Are is an independently selected arylene group, such as a phenylene or anthracene group,
n is an integer of from 1 to 4, and
Ar, $R_7$, $R_8$, and $R_9$ are independently selected aryl groups. In a typical embodiment, at least one of Ar, $R_7$, $R_8$, and $R_9$ is a polycyclic fused ring group, e.g., a naphthalene The various alkyl, alkylene, aryl, and arylene groups of the foregoing structural formulae (A), (B), (C), (D), can each in turn be substituted. Typical substituents include alkyl groups, alkoxy groups, aryl groups, aryloxy groups, and halogen such as fluoride, chloride, and bromide. The various alkyl and alkylene groups typically contain from about 1 to 6 carbon atoms. The cycloalkyl moieties can contain from 3 to about 10 carbon atoms, but typically contain five, six, or seven ring carbon atoms—e.g., cyclopentyl, cyclohexyl, and cycloheptyl ring structures. The aryl and arylene groups are usually phenyl and phenylene moieties.

The hole-transporting layer can be formed of a single or a mixture of aromatic tertiary amine compounds. Specifically, one may employ a triarylamine, such as a triarylamine satisfying the formula (B), in combination with a tetraaryldiamine, such as indicated by formula (D). When a triarylamine is employed in combination with a tetraaryldiamine, the latter is positioned as a layer interposed between the triarylamine and the electron injecting and transporting layer. Illustrative of useful aromatic tertiary amines are the following:

1,1-Bis(4-di-p-tolylaminophenyl)cyclohexane
1,1-Bis(4-di-p-tolylaminophenyl)-4-phenylcyclohexane
4,4'-Bis(diphenylamino)quadriphenyl
Bis(4-dimethylamino-2-methylphenyl)-phenylmethane
N,N,N-Tri(p-tolyl)amine
4-(di-p-tolylamino)-4'-[4(di-p-tolylamino)-styryl]stilbene
N,N,N',N'-Tetra-p-tolyl-4-4'-diaminobiphenyl
N,N,N',N'-Tetraphenyl-4,4'-diaminobiphenyl
N,N,N',N'-tetra-1-naphthyl-4,4'-diaminobiphenyl
N,N,N',N'-tetra-2-naphthyl-4,4'-diaminobiphenyl
N-Phenylcarbazole
4,4'-Bis[N-(1-naphthyl)-N-phenylamino]biphenyl
4,4'-Bis[N-(1-naphthyl)-N-(2-naphthyl)amino]biphenyl
4,4''-Bis[N-(1-naphthyl)-N-phenylamino]p-terphenyl
4,4'-Bis[N-(2-naphthyl)-N-phenylamino]biphenyl
4,4'-Bis[N-(3-acenaphthenyl)-N-phenylamino]biphenyl
1,5-Bis[N-(1-naphthyl)-N-phenylamino]naphthalene
4,4'-Bis[N-(9-anthryl)-N-phenylamino]biphenyl
4,4''-Bis[N-(1-anthryl)-N-phenylamino]-p-terphenyl
4,4'-Bis[N-(2-phenanthryl)-N-phenylamino]biphenyl
4,4'-Bis[N-(8-fluoranthenyl)-N-phenylamino]biphenyl
4,4'-Bis[N-(2-pyrenyl)-N-phenylamino]biphenyl
4,4'-Bis[N-(2-naphthacenyl)-N-phenylamino]biphenyl
4,4'-Bis[N-(2-perylenyl)-N-phenylamino]biphenyl
4,4'-Bis[N-(1-coronenyl)-N-phenylamino]biphenyl
2,6-Bis(di-p-tolylamino)naphthalene
2,6-Bis[di-(1-naphthyl)amino]naphthalene
2,6-Bis[N-(1-naphthyl)-N-(2-naphthyl)amino]naphthalene
N,N,N',N'-Tetra(2-naphthyl)-4,4''-diamino-p-terphenyl
4,4'-Bis{N-phenyl-N-[4-(1-naphthyl)-phenyl]amino}biphenyl
4,4'-Bis[N-phenyl-N-(2-pyrenyl)amino]biphenyl
2,6-Bis[N,N-di(2-naphthyl)amine]fluorine
1,5-Bis[N-(1-naphthyl)-N-phenylamino]naphthalene Another class of useful hole-transporting materials includes polycyclic aromatic compounds as described in EP 1 009 041. In addition, polymeric hole-transporting materials can be used such as poly(N-vinylcarbazole) (PVK), polythiophenes, polypyrrole, polyaniline, and copolymers such as poly(3,4-ethylenedioxythiophene)/poly(4-styrenesulfonate) also called PEDOT/PSS.

Light-Emitting Layer (LEL)

As more fully described in U.S. Pat. Nos. 4,769,292 and 5,935,721, the light-emitting layer (LEL) 109 of the organic EL element comprises a luminescent or fluorescent material where electroluminescence is produced as a result of electron-hole pair recombination in this region. The light-emitting layer can be comprised of a single material, but more commonly consists of a host material doped with a guest compound or compounds where light emission comes primarily from the dopant and can be of any color. The host materials in the light-emitting layer can be an electron-transporting material, as defined below, a hole-transporting material, as defined above, or another material or combination of materials that support hole-electron recombination. The dopant is usually chosen from highly fluorescent dyes, but phosphorescent compounds, e.g., transition metal complexes as described in WO 98/55561, WO 00/18851, WO 00/57676, and WO 00/70655 are also useful. Dopants are typically coated as 0.01 to 10% by weight into the host material.

An important relationship for choosing a dye as a dopant is a comparison of the bandgap potential which is defined as the energy difference between the highest occupied molecular orbital and the lowest unoccupied molecular orbital of the molecule. For efficient energy transfer from the host to the dopant molecule, a necessary condition is that the band gap of the dopant is smaller than that of the host material.

Host and emitting molecules known to be of use include, but are not limited to, those disclosed in U.S. Pat. No. 4,768,292, U.S. Pat. No. 5,141,671, U.S. Pat. No. 5,150,006, U.S. Pat. No. 5,151,629, U.S. Pat. No. 5,405,709, U.S. Pat. No. 5,484,922, U.S. Pat. No. 5,593,788, U.S. Pat. No. 5,645,948, U.S. Pat. No. 5,683,823, U.S. Pat. No. 5,755,999, U.S. Pat. No. 5,928,802, U.S. Pat. No. 5,935,720, U.S. Pat. No. 5,935,721, and U.S. Pat. No. 6,020,078.

Metal complexes of 8-hydroxyquinoline and similar derivatives (Formula E) constitute one class of useful host compounds capable of supporting electroluminescence, and are particularly suitable for light emission of wavelengths longer than 500 nm, e.g., green, yellow, orange, and red.

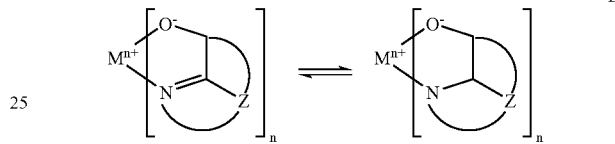

wherein
M represents a metal;
n is an integer of from 1 to 4; and
Z independently in each occurrence represents the atoms completing a nucleus having at least two fused aromatic rings.

From the foregoing it is apparent that the metal can be monovalent, divalent, trivalent, or tetravalent metal. The metal can, for example, be an alkali metal, such as lithium, sodium, or potassium; an alkaline earth metal, such as magnesium or calcium; an earth metal, such aluminum or gallium, or a transition metal such as zinc or zirconium. Generally any monovalent, divalent, trivalent, or tetravalent metal known to be a useful chelating metal can be employed.

Z completes a heterocyclic nucleus containing at least two fused aromatic rings, at least one of which is an azole or azine ring. Additional rings, including both aliphatic and aromatic rings, can be fused with the two required rings, if required. To avoid adding molecular bulk without improving on function the number of ring atoms is usually maintained at 18 or less.

Illustrative of useful chelated oxinoid compounds are the following:

CO-1: Aluminum trisoxine [alias, tris(8-quinolinolato)aluminum(III)]
CO-2: Magnesium bisoxine [alias, bis(8-quinolinolato)magnesium(II)]
CO-3: Bis[benzo {f}-8-quinolinolato]zinc (II)
CO-4: Bis(2-methyl-8-quinolinolato)aluminum(III)-μ-oxo-bis(2-methyl-8-quinolinolato)aluminum(III)
CO-5: Indium trisoxine [alias, tris(8-quinolinolato)indium]
CO-6: Aluminum tris(5-methyloxine) [alias, tris(5-methyl-8-quinolinolato) aluminum(III)]
CO-7: Lithium oxine [alias, (8-quinolinolato)lithium(I)]
CO-8: Gallium oxine [alias, tris(8-quinolinolato)gallium (III)]
CO-9: Zirconium oxine [alias, tetra(8-quinolinolato)zirconium(IV)]

CO-10: Bis(2-methyl-8-quinolinato)-4-phenylphenolatoaluminum(III)

Derivatives of 9,10-di-(2-naphthyl)anthracene (Formula F) constitute one class of useful hosts capable of supporting electroluminescence, and are particularly suitable for light emission of wavelengths longer than 400 nm, e.g., blue, green, yellow, orange or red.

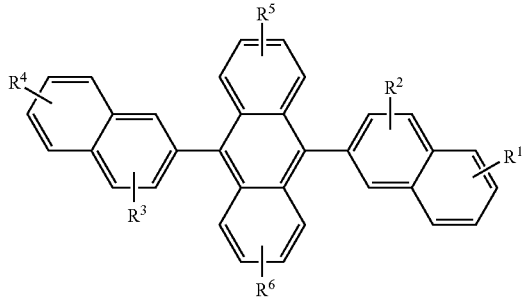

F wherein: $R^1$, $R^2$, $R^3$, $R^4$, $R^5$, and $R^6$ represent hydrogen or one or more substituents selected from the following groups:
Group 1: hydrogen, alkyl and alkoxy groups typically having from 1 to 24 carbon atoms;
Group 2: a ring group, typically having from 6 to 20 carbon atoms;
Group 3: the atoms necessary to complete a carbocyclic fused ring group such as naphthyl, anthracenyl, pyrenyl, and perylenyl groups, typically having from 6 to 30 carbon atoms;
Group 4: the atoms necessary to complete a heterocyclic fused ring group such as furyl, thienyl, pyridyl, and quinolinyl groups, typically having from 5 to 24 carbon atoms;
Group 5: an alkoxyamino, alkylamino, and arylamino group typically having from 1 to 24 carbon atoms; and
Group 6: fluorine, chlorine, bromine and cyano radicals.

Illustrative examples include 9,10-di-(2-naphthyl)anthracene and 2-t-butyl-9,10-di-(2-naphthyl)anthracene. Other anthracene derivatives can be useful as a host in the LEL, including derivatives of 9,10-bis[4-(2,2-diphenylethenyl)phenyl]anthracene, and phenylanthracene derivatives as described in EP 681,019.

Benzazole derivatives (Formula G) constitute another class of useful hosts capable of supporting electroluminescence, and are particularly suitable for light emission of wavelengths longer than 400 nm, e.g., blue, green, yellow, orange or red.

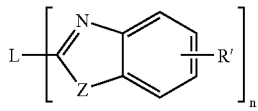

G where:
n is an integer of 3 to 8;
Z is —O, —NR or —S where R is H or a substituent; and
R' represents one or more optional substituents where R and each R' are H or alkyl groups such as propyl, t-butyl, and heptyl groups typically having from 1 to 24 carbon atoms;

carbocyclic or heterocyclic ring groups such as phenyl and naphthyl, furyl, thienyl, pyridyl, and quinolinyl groups and atoms necessary to complete a fused aromatic ring group typically having from 5 to 20 carbon atoms; and halo such as chloro, and fluoro;

L is a linkage unit usually comprising an alkyl or ary group which conjugately or unconjugately connects the multiple benzazoles together.

An example of a useful benzazole is 2,2',2"-(1,3,5-phenylene)tris[1-phenyl-1H-benzimidazole].

Distyrylarylene derivatives as described in U.S. Pat. No. 5,121,029 are also useful host materials in the LEL.

Desirable fluorescent dopants include groups derived from fused ring, heterocyclic and other compounds such as anthracene, tetracene, xanthene, perylene, rubrene, coumarin, rhodamine, quinacridone, dicyanomethylenepyran, thiopyran, polymethine, pyrilium thiapyrilium, and carbostyryl compounds. Illustrative examples of useful dopants include, but are not limited to, the following:

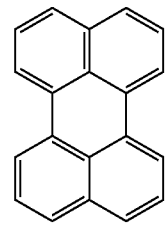

L1

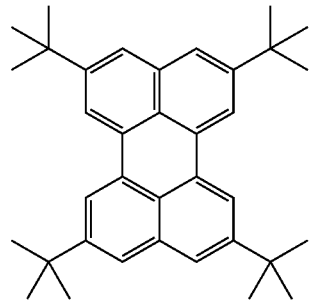

L2

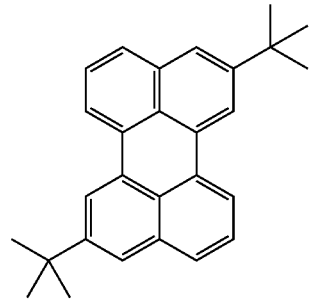

L3

-continued

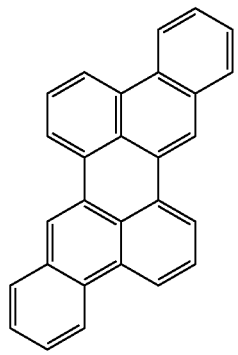

L4

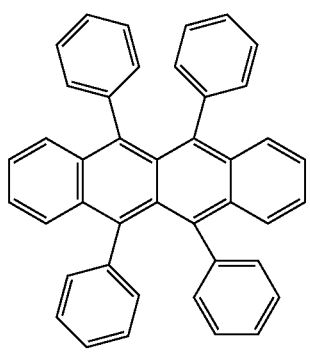

L5

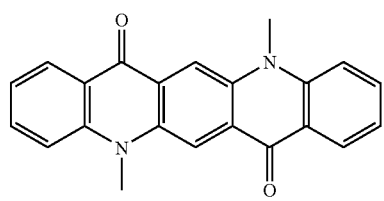

L6

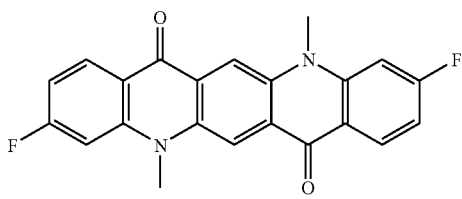

L7

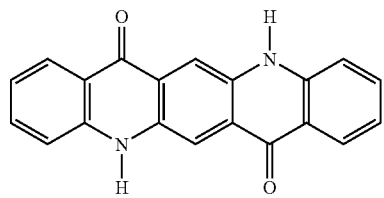

L8

-continued

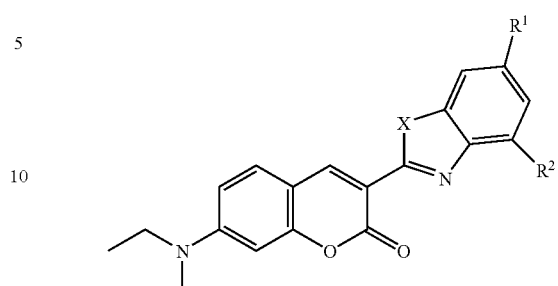

| | X | R1 | R2 |
|---|---|---|---|
| L9 | O | H | H |
| L10 | O | H | Methyl |
| L11 | O | Methyl | H |
| L12 | O | Methyl | Methyl |
| L13 | O | H | t-butyl |
| L14 | O | t-butyl | H |
| L15 | O | t-butyl | t-butyl |
| L16 | S | H | H |
| L17 | S | H | Methyl |
| L18 | S | Methyl | H |
| L19 | S | Methyl | Methyl |
| L20 | S | H | t-butyl |
| L21 | S | t-butyl | H |
| L22 | S | t-butyl | t-butyl |

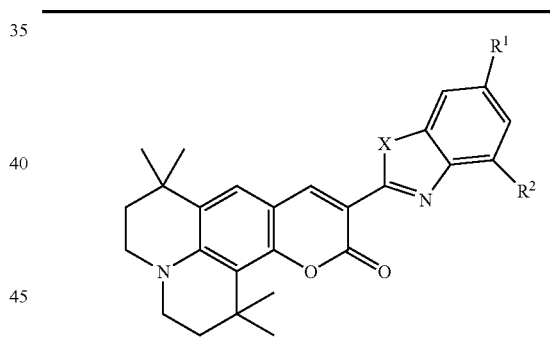

| | X | R1 | R2 |
|---|---|---|---|
| L23 | O | H | H |
| L24 | O | H | Methyl |
| L25 | O | Methyl | H |
| L26 | O | Methyl | Methyl |
| L27 | O | H | t-butyl |
| L28 | O | t-butyl | H |
| L29 | O | t-butyl | t-butyl |
| L30 | S | H | H |
| L31 | S | H | Methyl |
| L32 | S | Methyl | H |
| L33 | S | Methyl | Methyl |
| L34 | S | H | t-butyl |
| L35 | S | t-butyl | H |
| L36 | S | t-butyl | t-butyl |

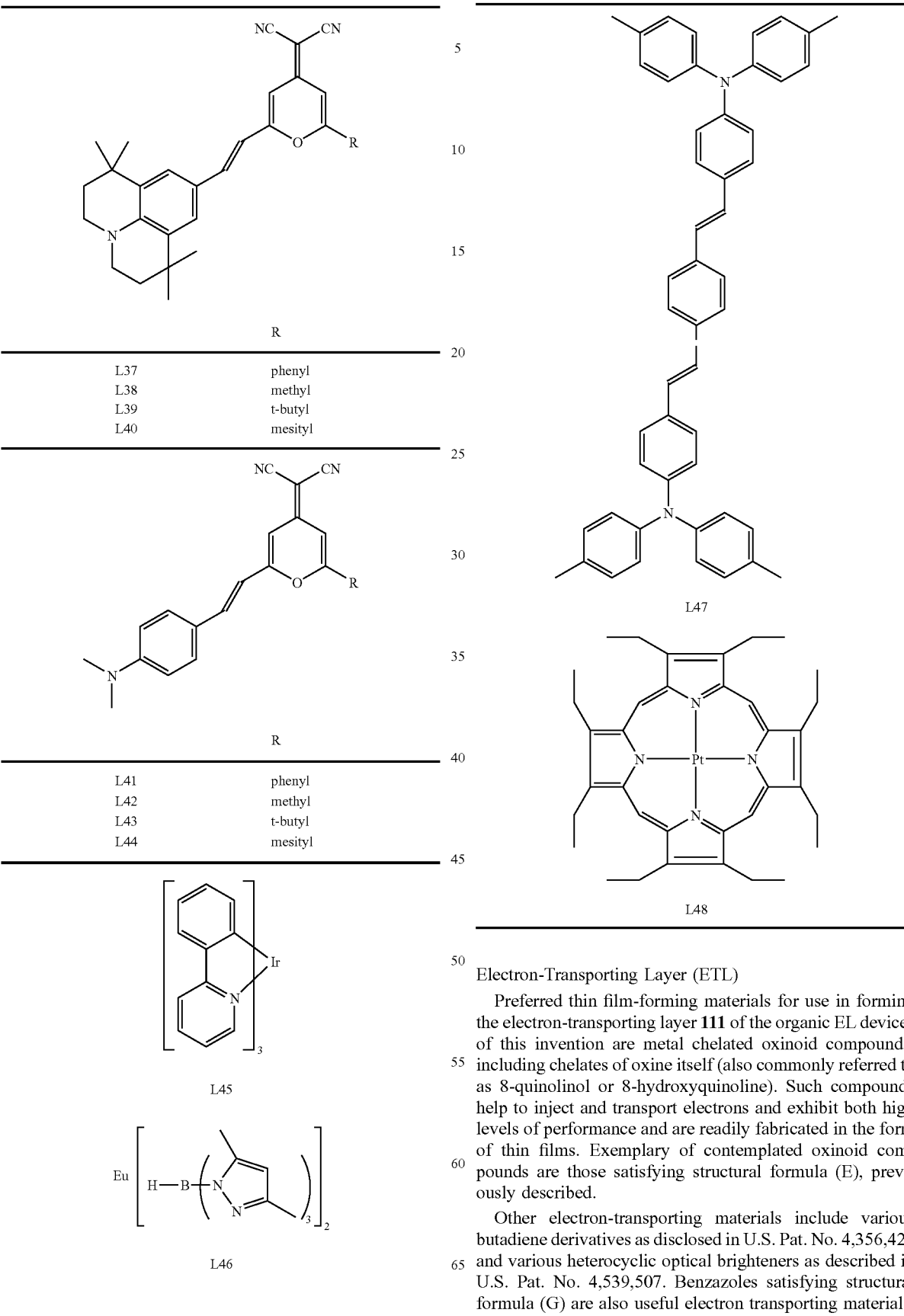

Electron-Transporting Layer (ETL)

Preferred thin film-forming materials for use in forming the electron-transporting layer 111 of the organic EL devices of this invention are metal chelated oxinoid compounds, including chelates of oxine itself (also commonly referred to as 8-quinolinol or 8-hydroxyquinoline). Such compounds help to inject and transport electrons and exhibit both high levels of performance and are readily fabricated in the form of thin films. Exemplary of contemplated oxinoid compounds are those satisfying structural formula (E), previously described.

Other electron-transporting materials include various butadiene derivatives as disclosed in U.S. Pat. No. 4,356,429 and various heterocyclic optical brighteners as described in U.S. Pat. No. 4,539,507. Benzazoles satisfying structural formula (G) are also useful electron transporting materials.

In some instances, layers 109 and 111 can optionally be collapsed into a single layer that serves the function of supporting both light emission and electron transportation.

Cathode

When light emission is through the anode, the cathode layer 113 used in this invention can be comprised of nearly any conductive material. Desirable materials have good film-forming properties to ensure good contact with the underlying organic layer, promote electron injection at low voltage, and have good stability. Useful cathode materials often contain a low work function metal (<4.0 eV) or metal alloy. One preferred cathode material is comprised of a Mg:Ag alloy wherein the percentage of silver is in the range of 1 to 20%, as described in U.S. Pat. No. 4,885,221. Another suitable class of cathode materials includes bilayers comprised of a thin layer of a low work function metal or metal salt capped with a thicker layer of conductive metal. One such cathode is comprised of a thin layer of LiF followed by a thicker layer of Al as described in U.S. Pat. No. 5,677,572. Other useful cathode materials include, but are not limited to, those disclosed in U.S. Pat. No. 5,059,861, U.S. Pat. No. 5,059,862, and U.S. Pat. No. 6,140,763.

When light emission is viewed through the cathode, the cathode must be transparent or nearly transparent. For such applications, metals must be thin or one must use transparent conductive oxides, or a combination of these materials. Optically transparent cathodes have been described in more detail in U.S. Pat. No. 5,776,623. Cathode materials can be deposited by evaporation, sputtering, or chemical vapor deposition. When needed, patterning can be achieved through many well known methods including, but not limited to, through-mask deposition, integral shadow masking as described in U.S. Pat. No. 5,276,380 and EP 0 732 868, laser ablation, and selective chemical vapor deposition.

Deposition of Organic Layers

The organic materials mentioned above are suitably deposited through sublimation, but can be deposited from a solvent with an optional binder to improve film formation. If the material is a polymer, solvent deposition is usually preferred. The material to be deposited by sublimation can be vaporized from a sublimator "boat" often comprised of a tantalum material, e.g., as described in U.S. Pat. No. 6,237,529, or can be first coated onto a donor sheet and then sublimed in closer proximity to the substrate. Layers with a mixture of materials can utilize separate sublimator boats or the materials can be pre-mixed and coated from a single boat or donor sheet. Patterned deposition can be achieved using shadow masks, integral shadow masks (U.S. Pat. No. 5,294,870), spatially-defined thermal dye transfer from a donor sheet (U.S. Pat. No. 5,851,709 and U.S. Pat. No. 6,066,357) and inkjet method (U.S. Pat. No. 6,066,357).

Encapsulation

Most OLED devices are sensitive to moisture and/or oxygen so they are commonly sealed in an inert atmosphere such as nitrogen or argon, along with a desiccant such as alumina, bauxite, calcium sulfate, clays, silica gel, zeolites, alkaline metal oxides, alkaline earth metal oxides, sulfates, or metal halides and perchlorates. Methods for encapsulation and desiccation include, but are not limited to, those described in U.S. Pat No. 6,226,890.

The entire contents of the patents and other publications referred to in this specification are incorporated herein by reference.

EXAMPLES

The invention and its advantages are further illustrated by the specific examples, which follow.

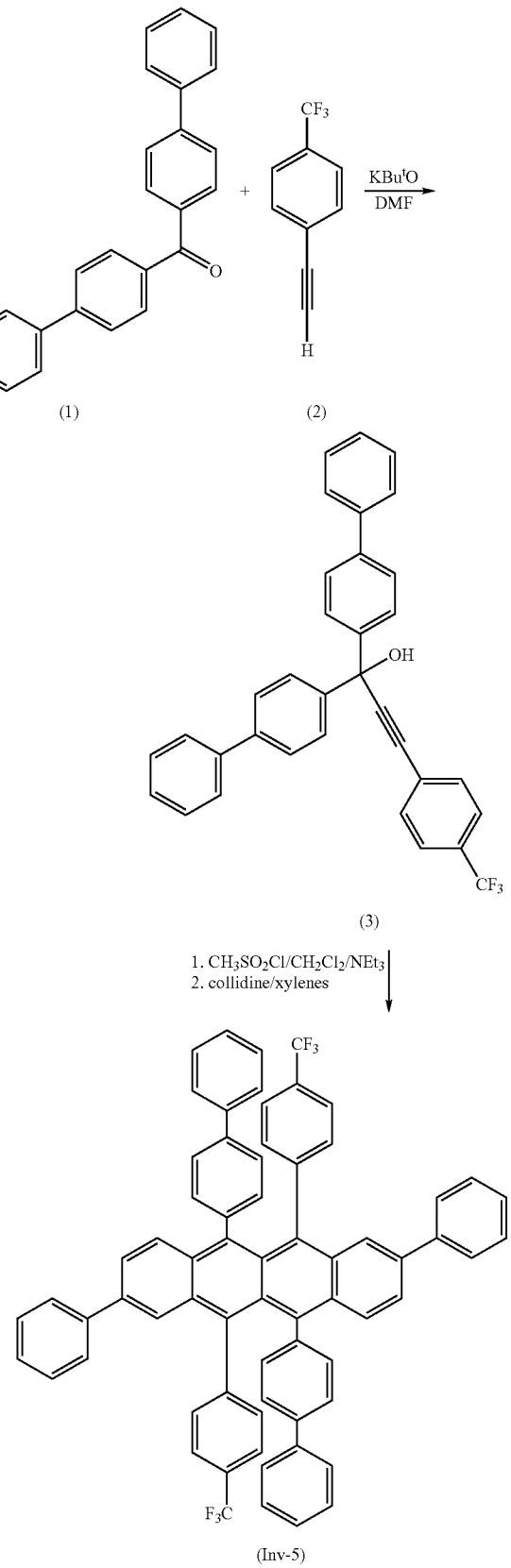

Example 1

Synthesis (Scheme 1)

Preparation of compound (3): Under a nitrogen atmosphere, acetylenic compound (2) (5.10 g, 30 mMole), was dissolved in dimethylformamide (DMF) (70 mL) and the solution cool to 0° C. Potassium t-butoxide (KBu$^t$O) (4.04 g, 36 mMole), was added and the mixture stirred well for approximately 15 minutes. To this mixture was then added the benzophenone (1) (10 g, 30 mMole). Stirring was continued at 0° C. for approximately 30 minutes and then allowed to come to room temperature over a 1-hour period. At the end of this time the solution was cooled to 0° C. and the reaction treated with saturated sodium chloride (20 mL). The mixture was then diluted with ethyl acetate, washed with 2N—HCl (×3), dried over MgSO$_4$, filtered and concentrated under reduced pressure. The crude product was dissolved in 20% ethyl acetate in heptane and subjected to pressure chromatography over silica gel eluting with the same solvent mixture. The main material was collected. Yield of compound (3), 10 g.

Preparation of Inventive Compound, Inv-5: Compound (3) (10 g, 19.82 mMole) was dissolved in methylene chloride (CH$_2$Cl$_2$) (70 mL), and stirred at 0° C. under a nitrogen atmosphere. To this solution was added triethylamine (NEt$_3$) (2.0 g, 19.82 mMole) and then treated drop by drop with methanesulfonyl chloride (CH$_3$SO$_2$Cl) (2.55 g, 19.82 mMole), keeping the temperature of the reaction in the range 0–5° C. After the addition the solution was stirred at 0° C. for 30 minutes and then allowed to warm to room temperature over 1 hour. The reaction was then heated to reflux, distilling off the methylene chloride solvent and gradually replacing it with xylenes (a total of 70 mL). When the internal temperature of the reaction reached 80° C., collidine (2.40 g, 19.82 mMole), dissolved in xylenes (10 mL) was added drop by drop over a 10-minute period. The temperature was then raised to 110° C. and held at this temperature for 4 hours. After this period the reaction was allowed to cool to approximately 80° C. and filtered. The filtrate was washed first with some xylenes and then methanol to give inventive compound Inv-5 as a bright red solid. Yield 3.6 g with a melting point of 360° C. The product may be further purified by sublimation (340° C. @ 200 milliTorr) with a N$_2$ carrier gas.

Example 2

Sublimation Temperatures

The sublimation temperatures at $5 \times 10^{-6}$ Torr needed to deposit the inventive and comparative dopants at 1% and 2%-wt. of the host are recorded in Table 1. This sublimation temperature is the temperature required to sublime a specific amount of material, recorded as thickness, onto the device at a specific rate and is given in Angstroms/sec., (A/s). For dopants at 1%-wt of host, this rate is 0.04 A/s and at 2%-wt it is 0.08 A/s. The samples shown in the table are divided into groups, each group with its own comparative dopant. Comp-1 is the comparative example for Inv-1 through Inv-4; Comp-2 is the comparative example for Inv-5, Inv-6 and Inv-9; Comp-3 is the comparative example for Inv-15; and Comp-4 is the comparative example for Inv-23 and Inv-24. The comparative dopants have the same basic structure as the inventive dopants in its group but without the fluorine or fluorine-containing group. Comp-1 is the parent rubrene. It is well known to those in the art.

The comparative compounds used in the invention are as follows:

TABLE 1

Comp-1

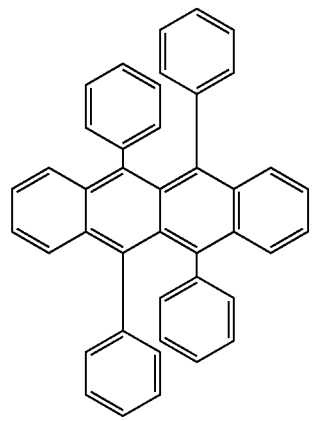

Comp-2

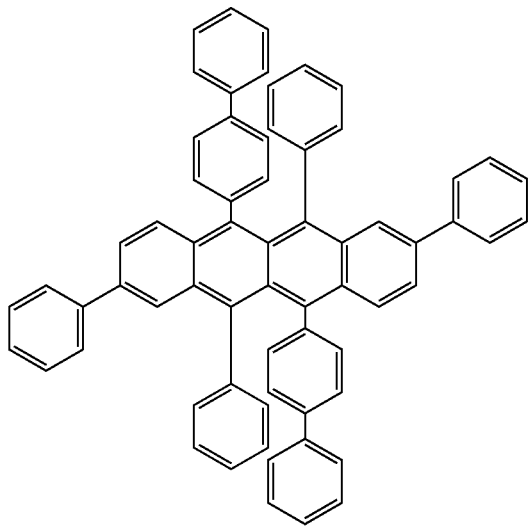

Comp-3

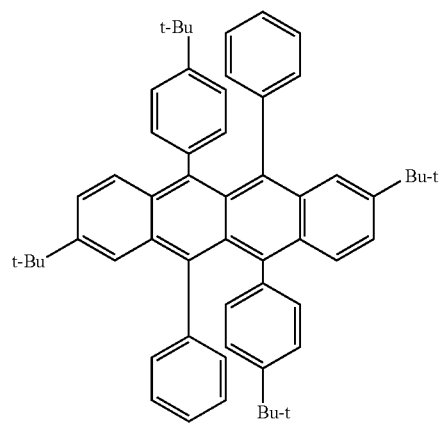

Comp-4

TABLE 1-continued

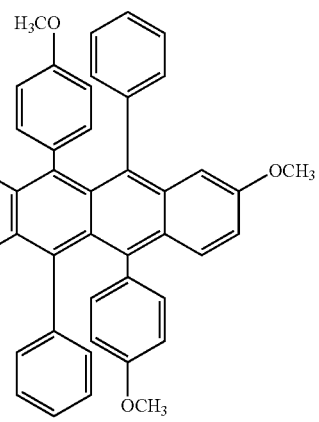

| Sample | Type | Dopant | Sublimation Temp (° C.) Dopant Level 1% | 2% |
|---|---|---|---|---|
| 1 | Comparative | Comp-1 | 211 | 218 |
| 2 | Inventive | Inv-1 | 184 | 188 |
| 3 | Inventive | Inv-2 | 200 | 208 |
| 4 | Inventive | Inv-3 | 200 | 210 |
| 5 | Inventive | Inv-4 | 190 | 203 |
| 6 | Comparative | Comp-2 | | melts |
| 7 | Inventive | Inv-5 | 300 | 308 |
| 8 | Inventive | Inv-6 | 297 | 298 |
| 9 | Inventive | Inv-9 | 301 | 208 |
| 10 | Comparative | Comp-3 | 230 | 241 |
| 11 | Inventive | Inv-15 | 214 | 224 |
| 12 | Comparative | Comp-4 | 221 | 232 |
| 13 | Inventive | Inv-23 | 214 | 219 |
| 14 | Inventive | Inv-24 | 206 | 215 |

It can be seen from Table 1 that the sublimation temperatures for each of the inventive dopants, samples 2–5, 7–9, 11, 13 and 14 is considerably lower than that of the comparative dopant in their respective group at both the 1% and 2% levels. In sample 6, the comparative dopant Comp-2 did not sublime but melted.

Example 3

EL Device Fabrication—Inventive Example

An EL device satisfying the requirements of the invention was constructed as Sample 15 in the following manner:

A glass substrate coated with an 85 nm layer of indium-tin oxide (ITO) as the anode was sequentially ultrasonicated in a commercial detergent, rinsed in deionized water, degreased in toluene vapor and exposed to oxygen plasma for about 1 min.

a) Over the ITO was deposited a 1 nm fluorocarbon (CFx) hole-injecting layer (HIL) by plasma-assisted deposition of $CHF_3$.

b) A hole-transporting layer (HTL) of N,N'-di-1-naphthalenyl-N,N'-diphenyl-4,4'-diaminobiphenyl (NPB) having a thickness of 150 nm was then evaporated from a tantalum boat.

c) A 37.5 nm light-emitting layer (LEL) of tris(8-quinolinolato)aluminum (III) ($AlQ_3$) and Inv-1 (2%-wt, see Table 2) were then deposited onto the hole-transporting layer. These materials were also evaporated from tantalum boats.

d) A 37.5 nm electron-transporting layer (ETL) of tris(8-quinolinolato)aluminum (III) ($AlQ_3$) was then deposited onto the light-emitting layer. This material was also evaporated from a tantalum boat.

e) On top of the $AlQ_3$ layer was deposited a 220 nm cathode formed of a 10:1 volume ratio of Mg and Ag.

The above sequence completed the deposition of the EL device. The device was then hermetically packaged in a dry glove box for protection against ambient environment.

Samples 16 through 18 were EL devices incorporating Inv-2 through Inv-4. Samples 19 through 21 were EL devices incorporating Inv-5, Inv-6 and Inv-9. Sample 22 was the EL device incorporating Inv-15 and samples 23 and 24 were EL devices incorporating Inv-23 and Inv-24. Samples 16 through 24 were fabricated in an identical manner, maintaining the same device architecture and at the same level, 2%-wt of the host, as sample 15, the example incorporating Inv-1. The cells thus formed were tested for emission $\lambda_{max}$ and efficiency (in the form of luminance yield), and the results are listed in Table 2.

TABLE 2

| Sample | Type | Host | Dopant (2%) | $\lambda_{max}$ (nm) (Device) | $\lambda_{max}$ (nm) (soln.) | Efficiency (cd/A)[1] |
|---|---|---|---|---|---|---|
| 15 | Inventive | $ALQ_3$ | Inv-1 | 552 | 538 | 6.22 |
| 16 | Inventive | " | Inv-2 | 560 | 552 | 7.15 |
| 17 | Inventive | " | Inv-3 | 560 | 550 | 8.4 |
| 18 | Inventive | " | Inv-4 | 560 | 552 | 7.68 |
| 19 | Inventive | " | Inv-5 | 580 | 576 | 7.78 |
| 20 | Inventive | " | Inv-6 | 564 | 576 | 4.96 |
| 21 | Inventive | " | Inv-9 | 576 | 572 | 7.62 |
| 22 | Inventive | " | Inv-15 | 560 | 570 | 7.55 |
| 23 | Inventive | " | Inv-23 | 584 | 592 | 6.92 |
| 24 | Inventive | " | Inv-24 | 572 | 588 | 6.95 |

[1]Luminance yields reported at 20 mA/cm².

As can be seen from Table 2, all tested EL devices incorporating the dopants of the invention at 2%-wt of the host, demonstrated good luminance yields. The dopants of the invention exhibit yellow to red electroluminescence with $\lambda_{max}$ values ranging from 538–592 nm in ethyl acetate solution and from 552–584 nm in doped EL devices.

PARTS LIST

101 Substrate
103 Anode
105 Hole-Injecting layer (HIL)
107 Hole-Transporting layer (HTL)
109 Light-Emitting layer (LEL)
111 Electron-Transporting layer (ETL)
113 Cathode

What is claimed is:

1. An OLED device comprising a light-emitting layer (LEL) containing a host and an emitting dopant located between a cathode and an anode wherein the dopant is a naphthacene derivative represented by formula (II):

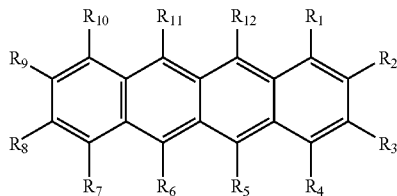

Formula (II)

wherein:

R$_5$, R$_6$, R$_{11}$ and R$_{12}$ are phenyl groups;

at least one of R$_1$, R$_2$, R$_3$, R$_4$, R$_5$, R$_6$, R$_7$, R$_8$, R$_9$, R$_{10}$, R$_{11}$ and R$_{12}$ is or contains a fluorine or a fluorine containing group:

provided that the remaining R$_1$, R$_2$, R$_3$, R$_4$, R$_5$, R$_6$, R$_7$, R$_8$, R$_9$, R$_{10}$, R$_{11}$ and R$_{12}$ are selected from hydrogen and substituent groups; and provided further that when exactly two fluorine containing groups are present said groups are not located at R$_5$ and R$_{12}$ or at R$_6$ and R$_{11}$, and further provided that the substituents are selected so that naphthacene derivative has a wavelength of maximum emission ($\lambda_{max}$) in ethyl acetate solution such that 520 nm$\leq \lambda_{max} \leq$650 nm.

2. The device of claim 1 comprising a further light-emitting compound to provide a white light emission.

3. The device of claim 2 further comprising a blue light-emitting compound to provide a white light emission.

4. The device of claim 2 further comprising a filter over-lying the device.

5. The device of claim 2 wherein the layer comprises a host and emitting dopant where the dopant is present in an amount of up to 10%-wt of the host.

6. The device of claim 5 wherein the emitting dopant is present in an amount of 0.1–5.0%-wt of the host.

7. The device of claim 1 wherein the emitting dopant is represented by formula (III):

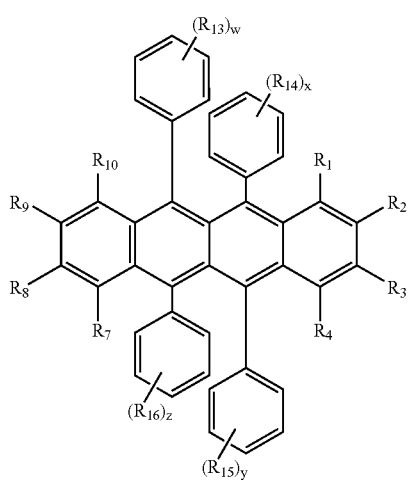

Formula (III)

wherein:

W, X, Y and Z are independently 0–5;

R$_{13}$, R$_{14}$, R$_{15}$, and R$_{16}$ are selected from hydrogen and substituent groups; and provided further that when exactly two fluorine or fluorine containing groups are present said groups are not located at R$_{14}$ and R$_{15}$ or at R$_{13}$ and R$_{16}$.

8. The device of claim 7 wherein the emitting dopant is represented by formula (IV):

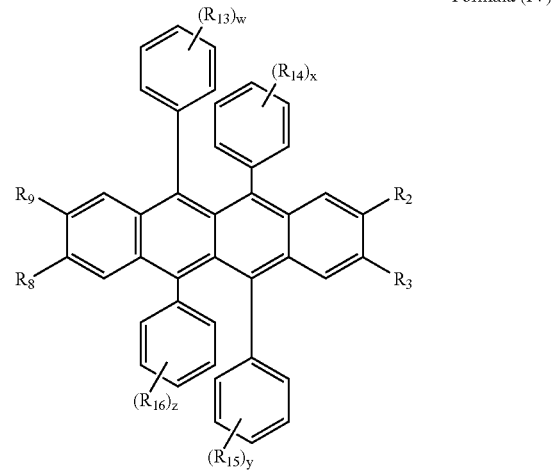

Formula (IV)

wherein:

W, X, Y and Z are independently 0–5;

at least one of R$_2$, R$_3$, R$_8$, R$_9$, R$_{13}$, R$_{14}$, R$_{15}$, and R$_{16}$ is fluorine or a fluorine containing group:

provided that the remaining R$_2$, R$_3$, R$_8$, R$_9$, R$_{13}$, R$_{14}$, R$_{15}$, and R$_{16}$ are selected from hydrogen and substituent groups;

provided further that when exactly two fluorine or fluorine containing groups are present said groups are not located at R$_{14}$ and R$_{15}$ or at R$_{13}$ and R$_{16}$.

9. The device of claim 8 wherein the emitting dopant is represented by formula (V):

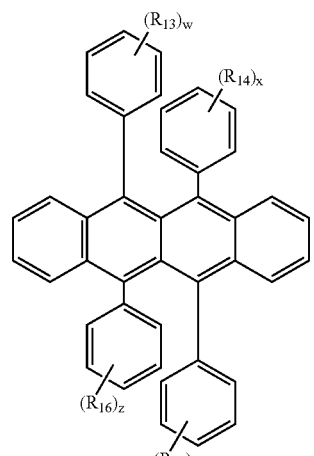

Formula (V)

wherein:

W, X, Y and Z are independently 0–5;

at least one of R$_{13}$, R$_{14}$, R$_{15}$, and R$_{16}$ is fluorine or a fluorine containing group;

provided that the remaining R$_{13}$, R$_{14}$, R$_{15}$, and R$_{16}$ are selected from hydrogen and substituent groups;

provided further that when exactly two fluorine or fluorine containing groups are present said groups are not located at $R_{14}$ and $R_{15}$ or at $R_{13}$ and $R_{16}$.

10. The device of claim 7 wherein the layer comprises a host and dopant where the dopant is present in an amount of up to 10%-wt of the host.

11. The device of claim 10 wherein the dopant is present in an amount of 0.1–5.0%-wt of the host.

12. The device of claim 7 comprising a further compound to provide a white light emission.

13. The device of claim 12 further comprising a blue light-emitting compound to provide a white light emission.

14. The device of claim 12 further comprising a filter over-lying the device.

15. A light-emitting display containing the OLED device of claim 7.

16. The device of claim 1 wherein the emitting dopant is represented by formula (VI):

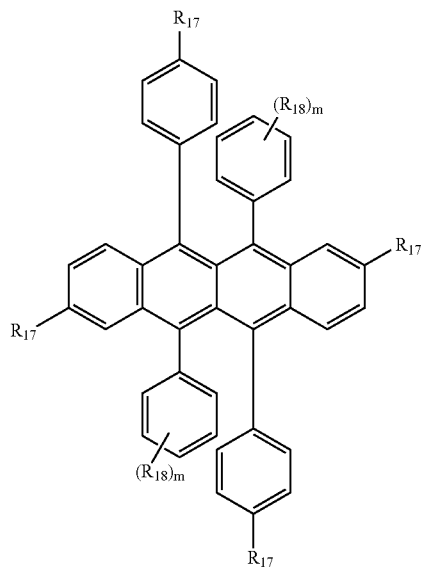

Formula (VI)

wherein:
$R_{18}$, is fluorine or a fluorine containing group:
$R_{17}$ is a substituent;
m is 0–5.

17. The device of claim 16 wherein $R_{17}$ and $R_{18}$ are selected from alkyl, alkoxy, acetylenic, alkenyl, cyano, carbocylic, fluoro, heterocyclic, trifluoromethyl, pentafluoroethyl and fluorinated-phenyl groups and at least one of $R_{17}$ and $R_{18}$ is fluorine or a fluorine containing group.

18. The device of claim 17 wherein $R_{17}$ and $R_{18}$ are selected from alkyl, alkoxy, carbocylic, fluoro, trifluoromethyl, pentafluoroethyl and fluorinated-phenyl groups and at least one of $R_{17}$ and $R_{18}$ is fluorine or a fluorine containing group.

19. The device of claim 17 wherein $R_{17}$ and $R_{18}$ are selected from tert-butyl, methoxy, phenyl, fluoro, trifluoromethyl, pentafluoroethyl and fluorinated-phenyl groups and at least one of $R_{17}$ and $R_{18}$ is fluorine or a fluorine containing group.

20. The device of claim 1 wherein at least one of $R_1$, $R_2$, $R_3$, $R_4$, $R_5$, $R_6$, $R_7$, $R_8$, $R_9$, $R_{10}$, $R_{11}$ and $R_{12}$ is selected from alkyl, aromatic carbocyclic and aromatic heterocyclic groups containing fluorine or fluorine containing groups.

21. The device of claim 20 wherein at least one of $R_1$, $R_2$, $R_3$, $R_4$, $R_5$, $R_6$, $R_7$, $R_8$, $R_9$, $R_{10}$, $R_{11}$ and $R_{12}$ is an aromatic carbocyclic group containing fluorine or fluorine containing groups.

22. The device of claim 1 wherein the host is an amine compound.

23. The device of claim 1 wherein the host comprises N,N'-di-1-naphthalenyl-N,N'-diphenyl-4,4'-diaminobiphenyl.

24. The device of claim 1 wherein the substituents are selected to provide an emitted light having an orange-red hue.

25. The device of claim 1 wherein the substituents are selected to provide a reduced loss of initial luminance compared to the device containing no naphthacene compound.

26. The device of claim 1 wherein the naphthacene compound is selected from the following:

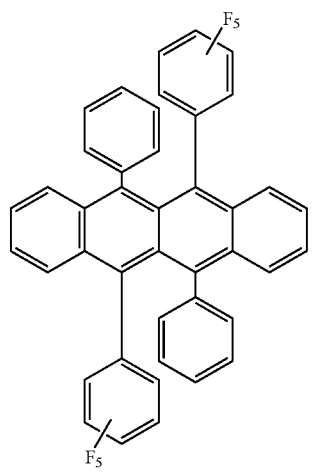

Inv-1

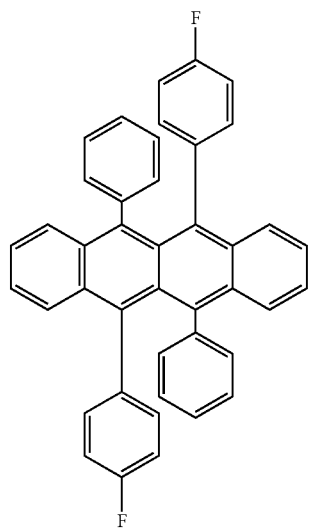

Inv-2

-continued
Inv-3
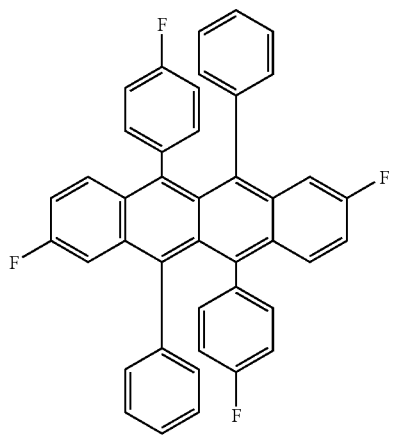
Inv-4
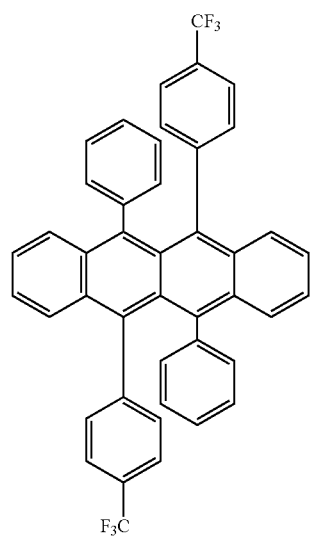
Inv-5
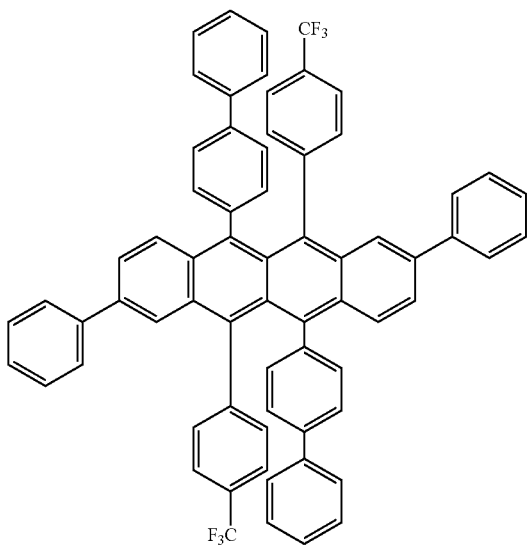
-continued
Inv-6
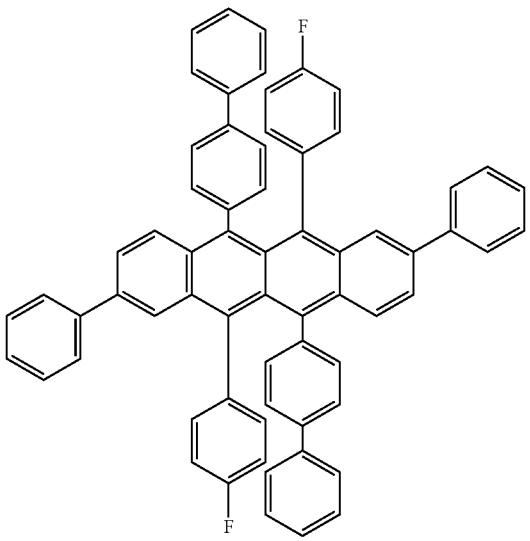
Inv-7
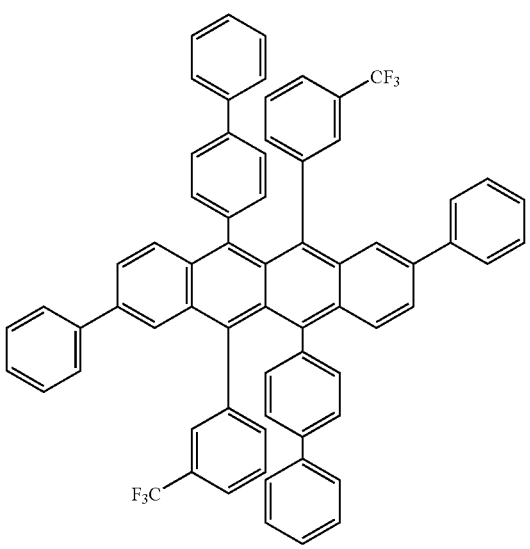
Inv-8
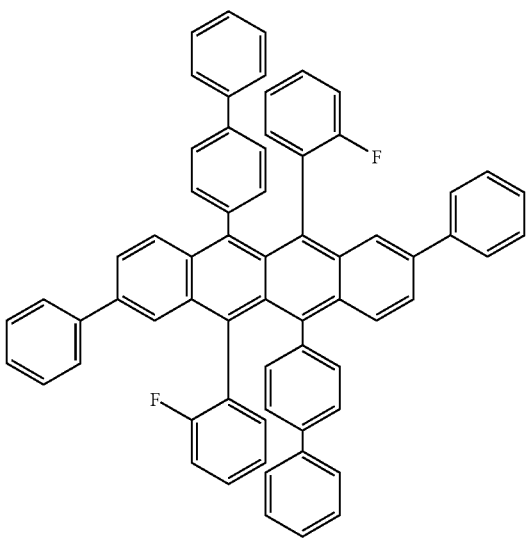

Inv-9
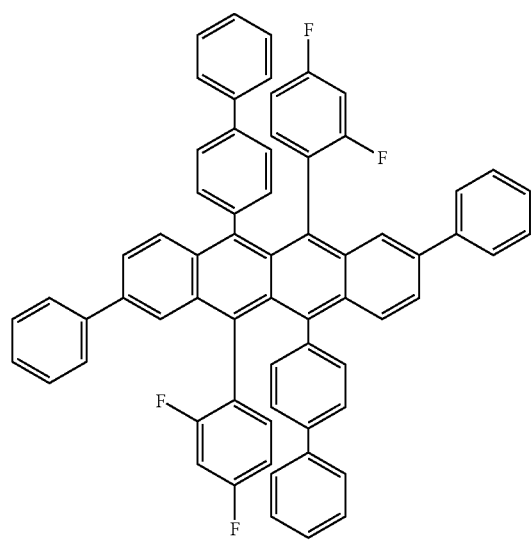
Inv-11
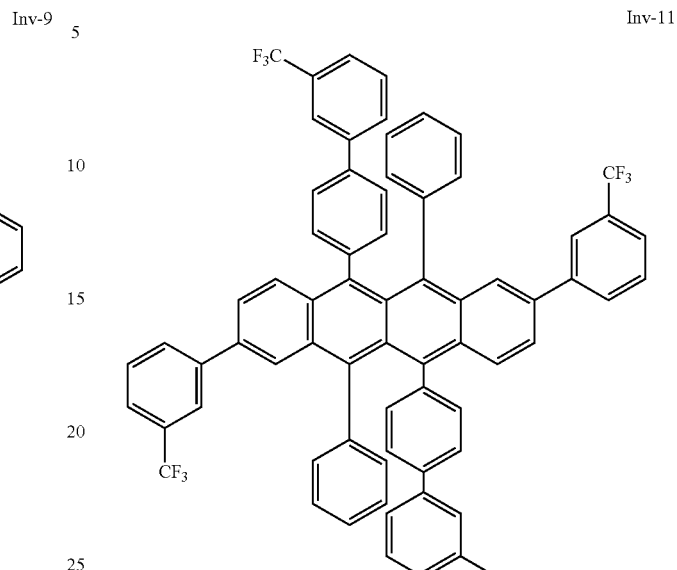
Inv-10
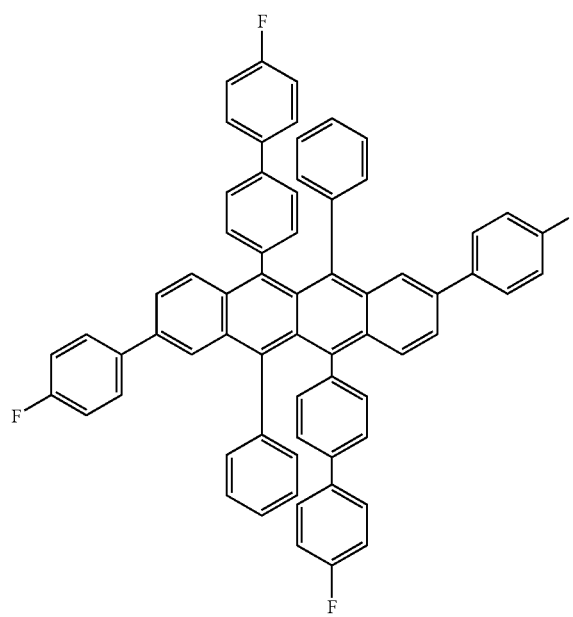
Inv-12
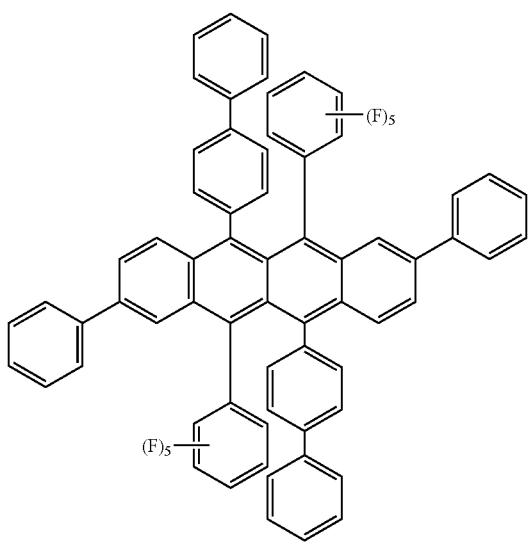

Inv-13
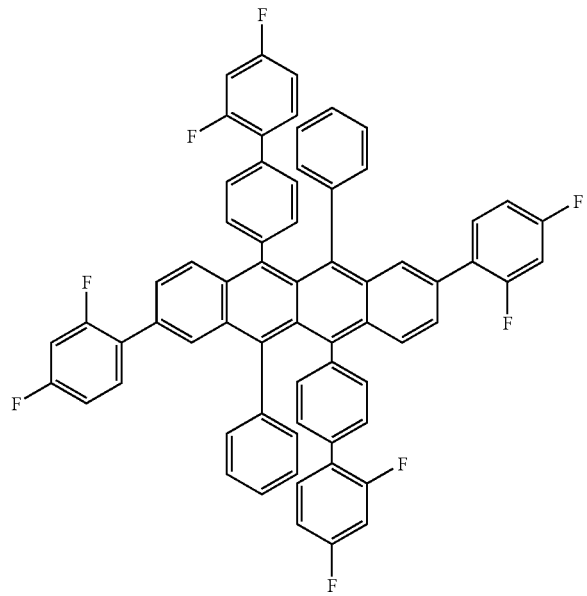
Inv-14
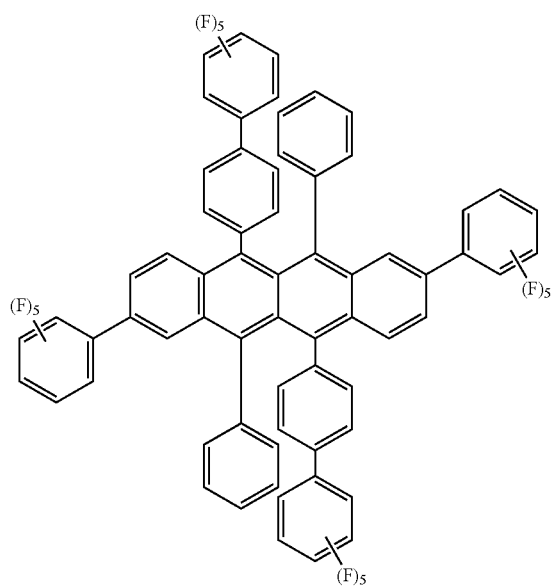
Inv-15
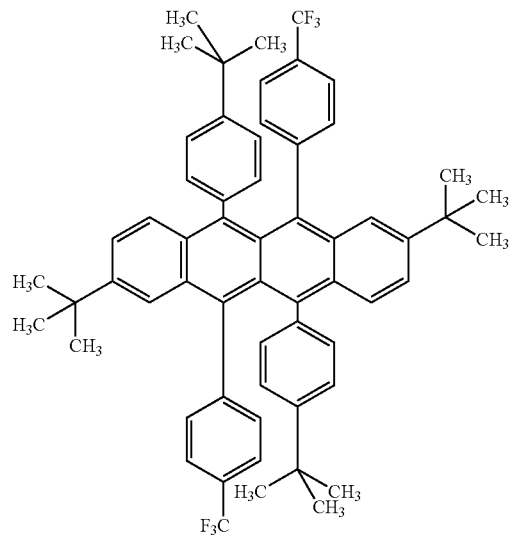
Inv-16
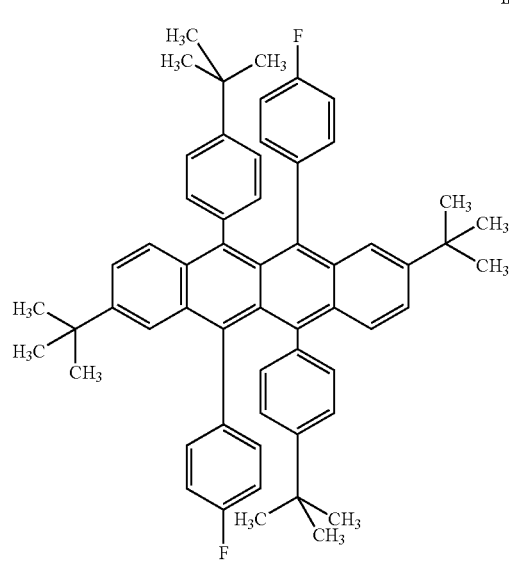
Inv-17
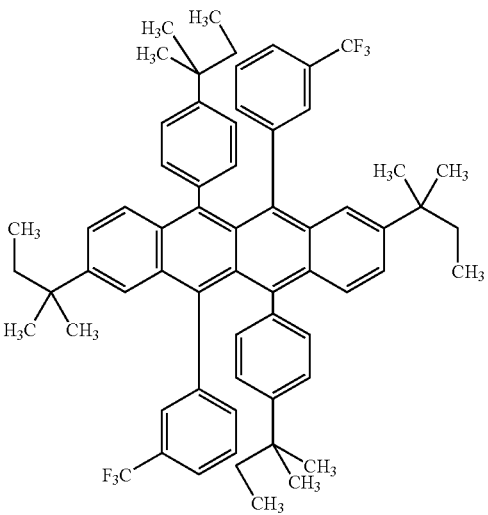

-continued
Inv-18
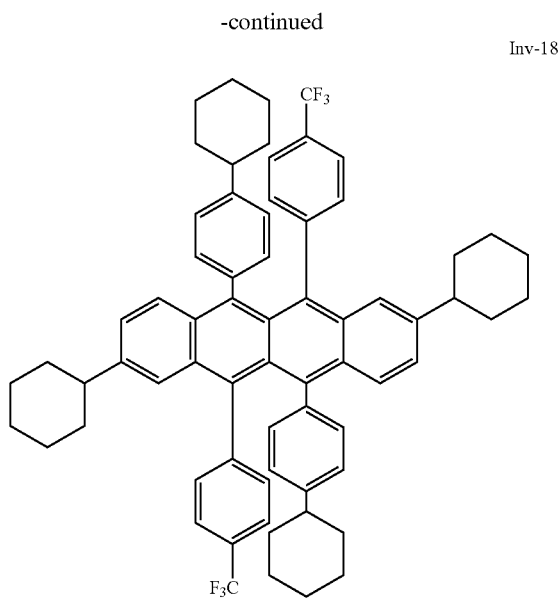
Inv-19
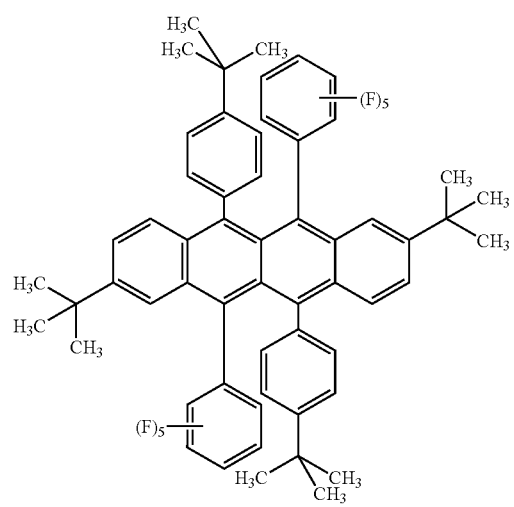
Inv-20
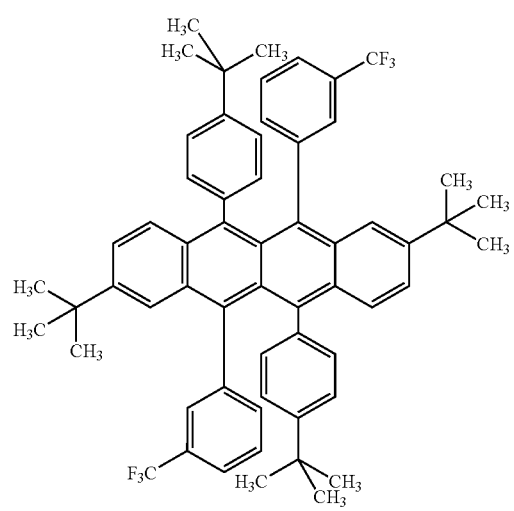
-continued
Inv-21
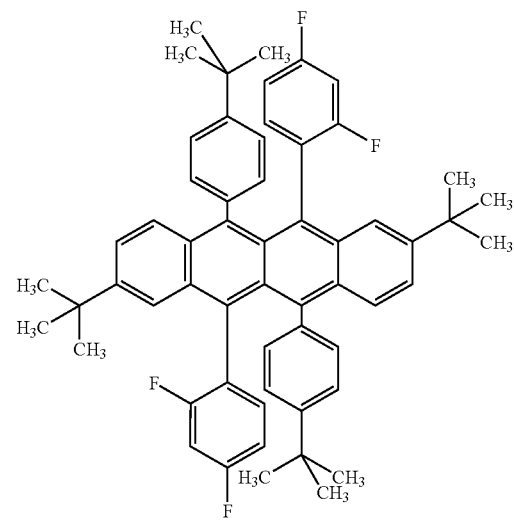
Inv-22
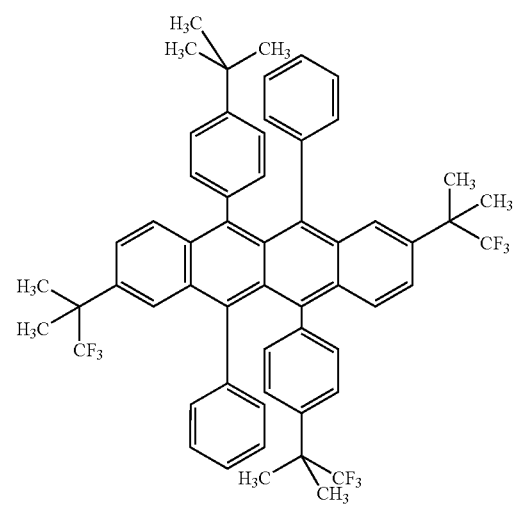
Inv-23
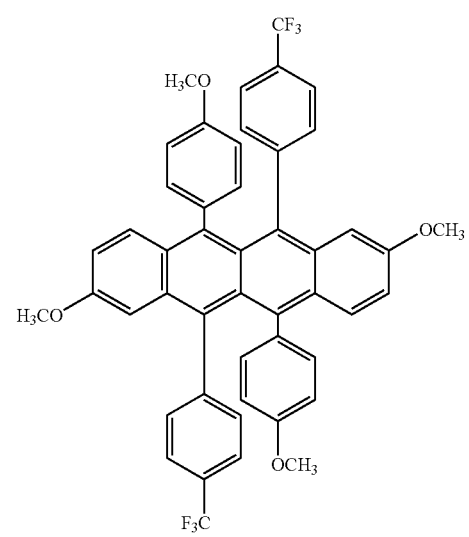

-continued
Inv-24
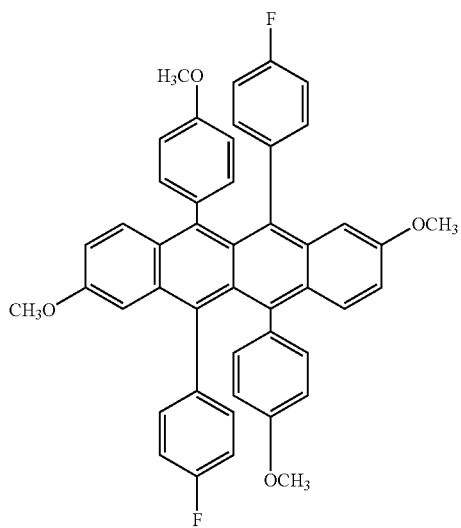
Inv-25
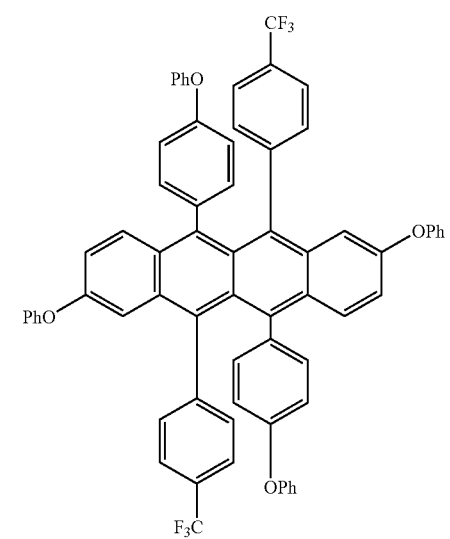
Inv-26
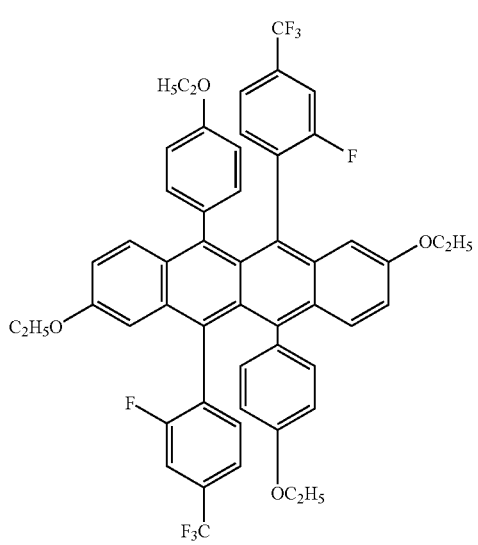
-continued
Inv-27
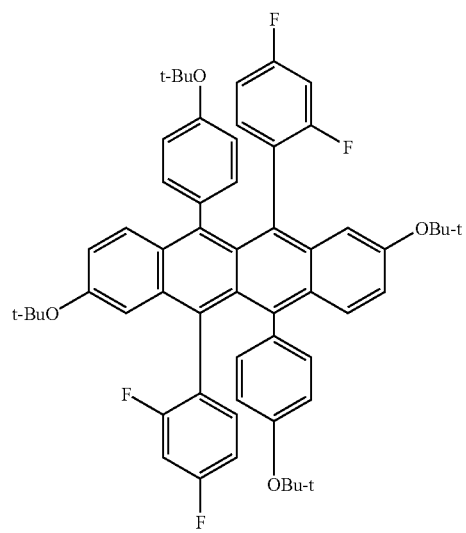
Inv-28
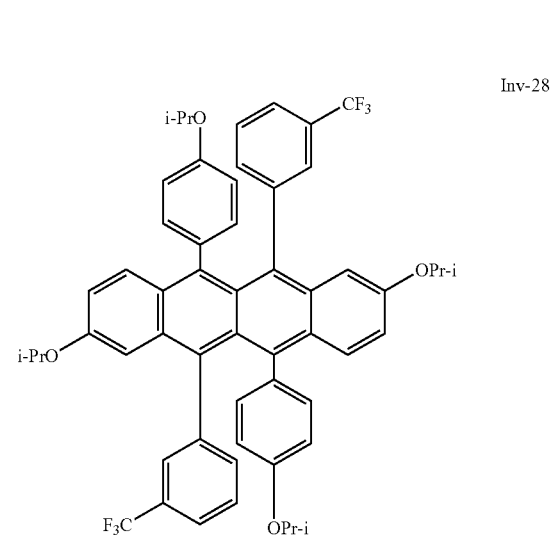
Inv-29
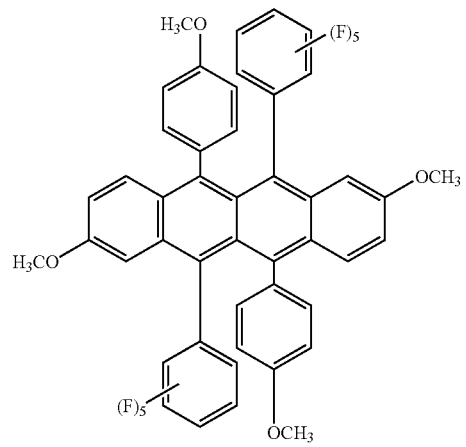

-continued

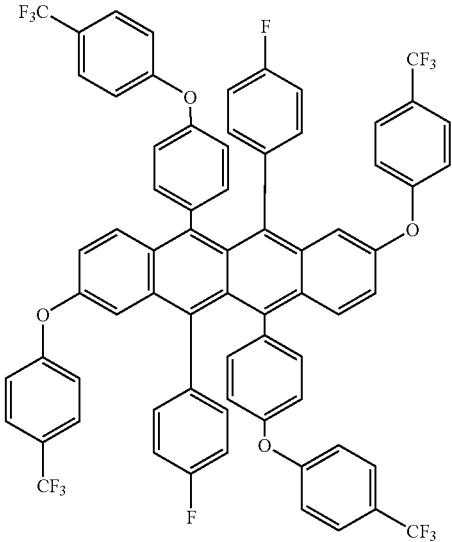
Inv-30

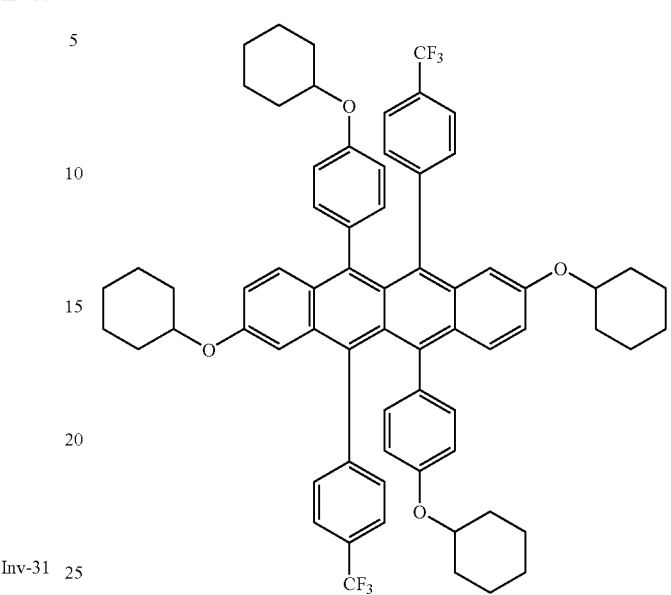
Inv-33

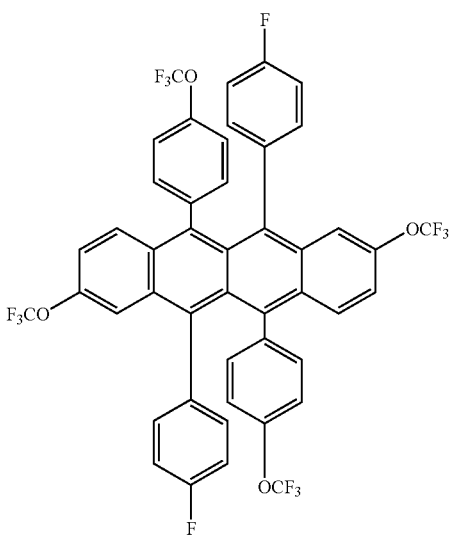
Inv-31

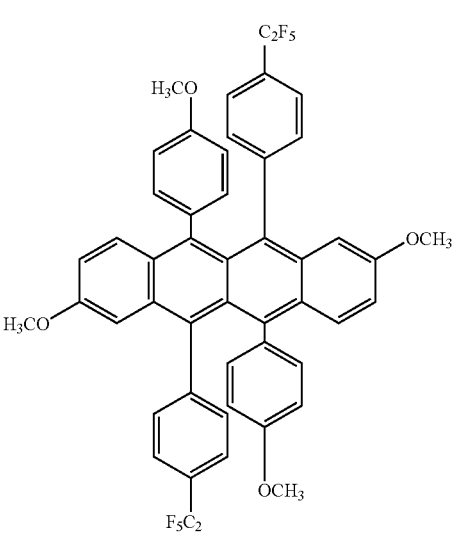
Inv-32

Inv-34

27. An OLED device of claim 1 wherein the naphthacene derivative has a wavelength of maximum emission ($\lambda_{max}$) in ethyl acetate solution such that 530 nm $\leq \lambda_{max} \leq$ 625 nm.

28. A light emitting device containing the OLED device of claim 1.

29. A method of emitting light comprising subjecting the device of claim 1 to an applied voltage.

30. The device of claim 1 wherein: either
   a) the sublimation temperature of said naphthacene derivative is lower by at least 5° C. than the derivative without fluorine or fluorine containing groups; or
   b) the naphthacene derivative sublimes and the derivative without the fluorine or fluorine containing groups melts.

31. An OLED device of claim 30 wherein the naphthacene derivative has a sublimation temperature of at least 10° C. lower than that of the naphthacene without fluorine or fluorine containing groups.

32. An OLED device of claim 31 wherein the naphthacene derivative has a sublimation temperature of at least 15° C. lower than that of the naphthacene without fluorine or fluorine containing groups.

33. An OLED device of claim 31 wherein the naphthacene derivative has a sublimation temperature of at least 20° C. lower than that of the naphthacene without fluorine or fluorine containing groups.

* * * * *